United States Patent
Hillman et al.

(10) Patent No.: US 9,260,488 B2
(45) Date of Patent: Feb. 16, 2016

(54) REPLACEMENT THERAPY FOR DENTAL CARIES

(71) Applicants: Oragenics, Inc., Alachua, FL (US); The Texas A&M University System, College Station, TX (US)

(72) Inventors: Jeffrey D. Hillman, Gainesville, FL (US); James Leif Smith, College Station, TX (US); Shawanda R. Wilson-Stanford, College Station, TX (US)

(73) Assignees: Oragenics, Inc., Alachua, FL (US); Texas A&M University, College Station, TX (US)

( * ) Notice: Subject to any disclaimer, the term of this patent is extended or adjusted under 35 U.S.C. 154(b) by 0 days.

(21) Appl. No.: 14/381,524

(22) PCT Filed: Feb. 22, 2013

(86) PCT No.: PCT/US2013/027340
§ 371 (c)(1),
(2) Date: Aug. 27, 2014

(87) PCT Pub. No.: WO2013/130351
PCT Pub. Date: Sep. 6, 2013

(65) Prior Publication Data
US 2015/0044146 A1 Feb. 12, 2015

Related U.S. Application Data

(60) Provisional application No. 61/603,693, filed on Feb. 27, 2012, provisional application No. 61/603,661, filed on Feb. 27, 2012.

(51) Int. Cl.

| | |
|---|---|
| *A61K 39/09* | (2006.01) |
| *A61K 49/00* | (2006.01) |
| *A61K 39/00* | (2006.01) |
| *C07K 14/195* | (2006.01) |
| *C07K 14/315* | (2006.01) |
| *A23G 4/12* | (2006.01) |
| *A23L 1/30* | (2006.01) |
| *A23L 2/52* | (2006.01) |
| *A61K 8/99* | (2006.01) |
| *A61K 35/744* | (2015.01) |
| *A61Q 11/00* | (2006.01) |
| *C12N 9/04* | (2006.01) |
| *A01N 25/34* | (2006.01) |
| *A01N 63/02* | (2006.01) |
| *A61K 38/16* | (2006.01) |
| *A61K 45/06* | (2006.01) |
| *A61K 39/02* | (2006.01) |
| *A61K 38/12* | (2006.01) |

(52) U.S. Cl.
CPC .............. *C07K 14/195* (2013.01); *A01N 25/34* (2013.01); *A01N 63/02* (2013.01); *A23G 4/123* (2013.01); *A23L 1/3014* (2013.01); *A23L 2/52* (2013.01); *A61K 8/99* (2013.01); *A61K 35/744* (2013.01); *A61K 38/164* (2013.01); *A61K 39/09* (2013.01); *A61K 45/06* (2013.01); *A61Q 11/00* (2013.01); *C07K 14/315* (2013.01); *C12N 9/0006* (2013.01); *A23V 2002/00* (2013.01); *A61K 38/12* (2013.01); *A61K 39/02* (2013.01); *A61K 2800/74* (2013.01); *C12Y 101/01001* (2013.01)

(58) Field of Classification Search
CPC ......... A61K 39/00; A61K 39/09; C07K 9/00; C07K 14/00; C07K 14/195; C07K 14/315
USPC ................... 424/9.1, 9.2, 184.1, 185.1, 234.1
See application file for complete search history.

(56) References Cited

U.S. PATENT DOCUMENTS

| 2006/0198793 A1 | 9/2006 | Hillman |
|---|---|---|
| 2009/0215985 A1 | 8/2009 | Kirichenko |

FOREIGN PATENT DOCUMENTS

| WO | 98/56411 | 6/1998 |
|---|---|---|
| WO | 03070919 A1 | 8/2003 |
| WO | 2008/151434 | 12/2008 |

OTHER PUBLICATIONS

Hillman et al., "Isolation of a *Streptococcus mutans* Strain Producing a Novel Bacteriocin", Infection and Immunity, 44 (1):141-144 (1984).
Hillman et al., "Modification of an effector strain for replacement therapy of dental caries to enable clinical safety trials", Journal of Applied Microbiology, 102:1209-1219 (2007).
Wilson-Stanford et al., "Oxidation of Lanthionines Renders the Lantibiotic Nisin Inactive", Applied and Environmental Microbiology, 75(5):1381-1387 (2009).
Hillman et al., "Evidence that L-(+)-Lactate Dehydrogenase Deficiency is Lethal in *Streptococcus mutans*", Infection and Immunity, 62(1):60-64 (1994).
Hillman et al., "Genetic and Physiological Analysis of the Lethal Effect of L-(+)_Lactate Dehydrogenase Deficiency in *Streptococcus mutans*: Complementation by Alcohol Dehydrogenase from Zymomonas mobils", Infection and Immunity, 64(10):4319-4323 (1996).

(Continued)

*Primary Examiner* — Rodney P Swartz
(74) *Attorney, Agent, or Firm* — McDonnell Boehnen Hulbert & Berghoff LLP

(57) ABSTRACT

The invention provides recombinant *Streptococcus mutans* strains that can be used to improve oral health. An embodiment of the invention provides a method of reducing the incidence or severity of dental caries in a dental caries-susceptible host comprising administering orally to the host an isolated recombinant *S. mutans* strain of the invention in an amount effective for replacement of dental caries-causing *S. mutans* host strains in the oral cavity of the host. The isolated recombinant *S. mutans* strain 10 can be contained in a mouthwash, toothpaste, chewing gum, floss, chewable tablet, food, or beverage.

10 Claims, 6 Drawing Sheets

(56) References Cited

OTHER PUBLICATIONS

Hillman et al. "Cloning and Expression of the Gene Encoding the Fructose-1,6-Diphosphate-Dependent L-(+)-Lactate Dehydrogenase of *Streptococcus mutans*", Infection and Immunity, 58(5):1290-1295 (1990).

Duncan et al., "DNA Sequence and In Vitro Mutagenesis of the Gene Encoding the Fructose-1,6-Diphosphate-Dependent L-(+)-Lactate Dehydrogenase of *Streptococcus mutans*", Infection and Immunity, 59(11):3930-3934 (1991).

Conway et al., "Cloning and Sequencing at the Alcohol Dehydrogenase II Gene from Zymomonas mobilis", Journal of Bacteriology, 169(6):2591-2597 (1987).

Hillman et al., "Construction and Characterization of an Effector Strain of *Streptococcus mutans* for Replacement Therapy of Dental Caries", Infection and Immunity, 68(2):543-549 (2000).

International Search Report for corresponding PCT application No. PCT/US2013/027340, dated May 31, 2013.

Chatterjee et al., "Biosynthesis and Mode of Action of Lantibiotics", Chem. Rev. 105:633-683 (2005).

Hillman, "Modification of an effector strain for replacement therapy of dental caries to enable clinical safety trials", Journal of Applied Microbiology, 102:1209-1219 (2007).

Hillman, "Colonization of the Human Oral Cavity", J. Dent Res, 66(6):1092-1094 (1987).

Hillman, "Genetically modified *Streptococcus mutans* for the prevention of dental caries", Antonie van Leeuwenhoek, 82:361-366 (2002).

Hillman, "The relationships between streptococcal species and periodontopathic bacteria in human dental plaque", Arch. oral. Biol., 30:791-795 (1985).

Hillman, "Interaction between wild-type, mutant and revertant forms of the bacterium *Streptococcus sanguis* and the bacterium Actionbacillus actinomycetemcomitans in vitro and in Gnotobiotic rat", Archs oral Biol., 33(6):395-401 (1988).

GenBank Accession No. M15394, dated Apr. 26, 1993.

Smith, "Structure and Dynamics of the Lantibiotic Mutacin 1140", Biochemistry, 42:10372-10384 (2003).

Socransky, "Associations between microbial species in subgingival plaque samples", Oral Microbiol Immunol., 3:1-7 (1988).

Gupta et al., "Use a Thorn to Draw Thorn' Replacement Therapy for Prevention of Dental Caries", International Journal of Clinical Pediatric Dentistry, 3(3):125-137 (2010).

Wang et al., "Interactions between Oral Bacteria: Inhibition of *Streptococcus*mutans *Bacteriocin*Production by *Streptococcus gordonii*", Applied and Environmental Microbiology, 71(1):354-362 (2005).

European Search Report for corresponding European application No. 13755436.6, dated Dec. 22, 2015.

EBI Accession No. AAB41196 dated Nov. 8, 1996.

Wild-type (native) MU1140

Schematic of Variations to MU1140
Abbreviations and symbols: ins=insertion and Δ= deletion.

Alignment of mutants to Wild-type Sequence

```
Wild-type      TTCAAAAGTTGG---AGCCTTTGT---ACGCCTGGTTGTGCAAGGACAGGTAGTTTCAATAGTTACTGTTGC
Phe1Gly        GGCAAAAGTTGG---AGCCTTTGT---ACGCCTGGTTGTGCAAGGACAGGTAGTTTCAATAGTTACTGTTGC
Phe1Ile        ATCAAAAGTTGG---AGCCTTTGT---ACGCCTGGTTGTGCAAGGACAGGTAGTTTCAATAGTTACTGTTGC
Trp4Ala        TTCAAAAGTGCA---AGCCTTTGT---ACGCCTGGTTGTGCAAGGACAGGTAGTTTCAATAGTTACTGTTGC
Trp4insAla     TTCAAAAGTTGGGCAAGCCTTTGT---ACGCCTGGTTGTGCAAGGACAGGTAGTTTCAATAGTTACTGTTGC
ΔTrp4          TTCAAAAGT------AGCCTTTGT---ACGCCTGGTTGTGCAAGGACAGGTAGTTTCAATAGTTACTGTTGC
Ser5Ala        TTCAAAAGTTGG---GCACTTTGT---ACGCCTGGTTGTGCAAGGACAGGTAGTTTCAATAGTTACTGTTGC
Cys7insAla     TTCAAAAGTTGG---AGCCTTTGTGCAACGCCTGGTTGTGCAAGGACAGGTAGTTTCAATAGTTACTGTTGC
Arg13Asp       TTCAAAAGTTGG---AGCCTTTGT---ACGCCTGGTTGTGCAGACACAGGTAGTTTCAATAGTTACTGTTGC Wild-type      SEQ ID NO:19
Phe1Gly        SEQ ID NO:20
Phe1Ile        SEQ ID NO:21
Trp4Ala        SEQ ID NO:22
Trp4insAla     SEQ ID NO:23
ΔTrp4          SEQ ID NO:24
Ser5Ala        SEQ ID NO:25
Cys7insAla     SEQ ID NO:26
Arg13Asp       SEQ ID NO:27
```

Figure 2

Figure 3: Primers Used for Mutagenesis of MU1140

| Oligonucleotide | Sequence (5' – 3') |
|---|---|
| SRWlanA_1 | A<u>GAATTC</u>AGGATGCTATCGCTGCTTTTTTTGTG (SEQ ID NO:1) |
| SRWlanA_2 | A<u>GAATTC</u>AGGAAAGTTGCCATATGGTTTTGTG (SEQ ID NO:2) |
| Phe1Gly_1 | GATCCAGATACTCGTGGCAAAAGTTGGAGCCTTTGTACG (SEQ ID NO:15) |
| Phe1Gly_2 | CAACTTTTGCCACGAGTATCTGGATCGTCGTTGC (SEQ ID NO:16) |
| Phe1Ile_1 | GATCCAGATACTCGTATCAAAAGTTGGAGCCTTTGTACG (SEQ ID NO:17) |
| Phe1Ile_2 | CAACTTTTGATACGAGTATCTGGATCGTCGTTGC (SEQ ID NO:18) |
| Trp4Ala_1 | GCAAGCCTTTGTACGCCTGGTTG (SEQ ID NO:3) |
| Trp4Ala_2 | ACAAAGGCTTGCACTTTTGAAACG (SEQ ID NO:4) |
| Trp4insAla_1 | GCAAGCCTTTGTACGCCTGGTTG (SEQ ID NO:5) |
| Trp4insAla_2 | CAAAGGCTTGCCCAACTTTTGAAACG (SEQ ID NO:6) |
| ΔTrp4_1 | ---AGCCTTTGTACGCCTGGTTG (SEQ ID NO:7) |
| ΔTrp4_2 | CGTACAAAGGCTACTTTTGAAACG (SEQ ID NO:8) |
| Dha5Ala_1 | GCACTTTGTACGCCTGGTTGTGC (SEQ ID NO:9) |
| Dha5Ala_2 | GGCGTACAAAGTGCCCAACTTTTGAA (SEQ ID NO:10) |
| Alas7InsAla_1 | GCAACGCCTGGTTGTGCAAGGAC (SEQ ID NO:11) |
| Alas7InsAla_2 | ACCAGGCGTTGCACAAAGGCTCC (SEQ ID NO:12) |
| Arg13Asp_1 | GACACAGGTAGTTTCAATAGTTAC (SEQ ID NO:13) |
| Arg13Asp_2 | GAAACTACCTGTGTCTGCACAACCAG (SEQ ID NO:14) |
| Outside primers are SRWlanA_1 and SRWlanA_2 and are homologous to the 5' and 3' flanking DNA. Underlined section represents the engineered EcoRI site. Mutations are either bolded or dashes. Numbering designates forward (1) and reverse (2) for primers. | |

Figure 4A-B: Zone of Inhibition Plate Assays

Bioactivity of Strains Producing Variants of MU1140 Compared to Wild-Type MU1140

| Variant Produced | Mean Area* (mm$^2$) | Standard Error of the Mean (SEM) | Ratio of Variant to Wild-Type Activities | Statistical Significance ($p$ value)[#] |
|---|---|---|---|---|
| MU1140 (wild-type) | 204.44 | 8.90 | - | - |
| Phe1Gly | 321.85 | 46.52 | 1.57 | <.001 |
| Phe1Ile | 372.78 | 75.90 | 1.82 | <.001 |
| Trp4Ala | 434.80 | 46.10 | 2.12 | <.001 |
| Trp4insAla | 212.37 | 24.70 | 1.04 | >.05 |
| ∇Trp4 | 217.56 | 35.37 | 1.06 | >.05 |
| Dha5Ala | 382.25 | 31.40 | 1.87 | <.001 |
| Ala$_s$7insAla | 109.41 | 9.74 | 0.54 | <.001 |
| Arg13Asp | 526.06 | 55.09 | 2.57 | <.001 |

* Based on 10 independent samples.
[#] Student's t Test

Figure 5

SEQUENCE LISTING

```
<160> NUMBER OF SEQ ID NOS: 30

<210> SEQ ID NO 1
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (3)..(7)
<220> FEATURE:
<221> NAME/KEY: MISC_FEATURE
<222> LOCATION: (5)..(5)
<223> OTHER INFORMATION: X is Dha amino acid
<220> FEATURE:
<221> NAME/KEY: MOD_RES
<222> LOCATION: (8)..(8)
<223> OTHER INFORMATION: Abu
<220> FEATURE:
<221> NAME/KEY: DISULFID
<222> LOCATION: (8)..(11)
<220> FEATURE:
<221> NAME/KEY: MISC_FEATURE
<222> LOCATION: (14)..(14)
<223> OTHER INFORMATION: X is Dhb amino acid
<220> FEATURE:
<221> NAME/KEY: DISULFID
<222> LOCATION: (16)..(21)
<220> FEATURE:
<221> NAME/KEY: MISC_FEATURE
<222> LOCATION: (19)..(21)
<223> OTHER INFORMATION: lanthionine bridge

<400> SEQUENCE: 1

Phe Lys Ala Trp Xaa Leu Ala Xaa Pro Gly Ala Ala Arg Xaa Gly Ala
1               5                   10                  15
```

Phe Asn Ala Tyr Ala
        20

<210> SEQ ID NO 2
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Ile or Gly
<220> FEATURE:
<221> NAME/KEY: DISULFID
<222> LOCATION: (3)..(8)
<220> FEATURE:
<221> NAME/KEY: MISC_FEATURE
<222> LOCATION: (4)..(4)
<223> OTHER INFORMATION: X is Trp, Ala or absent
<220> FEATURE:
<221> NAME/KEY: DISULFID
<222> LOCATION: (10)..(13)
<220> FEATURE:
<221> NAME/KEY: MISC_FEATURE
<222> LOCATION: (10)..(10)
<223> OTHER INFORMATION: X is Abu amino acid or Ala
<220> FEATURE:
<221> NAME/KEY: MISC_FEATURE
<222> LOCATION: (16)..(16)
<223> OTHER INFORMATION: X is Dhb amino acid or Ala
<220> FEATURE:
<221> NAME/KEY: DISULFID
<222> LOCATION: (18)..(23)
<220> FEATURE:
<221> NAME/KEY: MISC_FEATURE
<222> LOCATION: (21)..(23)
<223> OTHER INFORMATION: lanthionine bridge

<400> SEQUENCE: 2

Xaa Lys Ala Xaa Ala Ala Leu Ala Ala Xaa Pro Gly Ala Ala Asp Xaa
1               5                   10                  15

Gly Ala Phe Asn Ala Tyr Ala
            20

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
gcaagccttt gtacgcctgg ttg                                           23

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
acaaaggctt gcactttga aacg                                           24

<210> SEQ ID NO 5
<211> LENGTH: 23
<212> TYPE: DNA
<213> ORGANISM: Artificial Sequence
<220> FEATURE:
<223> OTHER INFORMATION: Synthetic -continued

```
<400> SEQUENCE: 5
gcaagccttt gtacgcctgg ttg                                          23

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
caaaggcttg cccaactttt gaaacg                                       26

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
agcctttgta cgcctggttg                                              20

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
cgtacaaagg ctacttttga aacg                                         24

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
gcactttgta cgcctggttg tgc                                          23

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
ggcgtacaaa gtgcccaact tttgaa                                       26

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
gcaacgcctg gttgtgcaag gac                                          23

<210> SEQ ID NO 12
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 12
accaggcgtt gcacaaaggc tcc                                              23

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
gacacaggta gtttcaatag ttac                                             24

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
gaaactacct gtgtctgcac aaccag                                           26

<210> SEQ ID NO 15
<211> LENGTH: 39
<212> TYPE: DNA
<213> ORGANISM: Artificial Sequence
<220> FEATURE:
<223> OTHER INFORMATION: Synthetic

<400> SEQUENCE: 15
gatccagata ctcgtggcaa aagttggagc ctttgtacg                             39

<210> SEQ ID NO 16
<211> LENGTH: 34
<212> TYPE: DNA
<213> ORGANISM: Artificial Sequence
<220> FEATURE:
<223> OTHER INFORMATION: Synthetic

<400> SEQUENCE: 16 caactttgc cacgagtatc tggatcgtcg ttgc                                   34

<210> SEQ ID NO 17
<211> LENGTH: 39
<212> TYPE: DNA
<213> ORGANISM: Artificial Sequence
<220> FEATURE:
<223> OTHER INFORMATION: Synthetic

<400> SEQUENCE: 17
gatccagata ctcgtatcaa aagttggagc ctttgtacg                             39

<210> SEQ ID NO 18
<211> LENGTH: 34
<212> TYPE: DNA
<213> ORGANISM: Artificial Sequence
<220> FEATURE:
<223> OTHER INFORMATION: Synthetic

<400> SEQUENCE: 18
```

```
caacttttga tacgagtatc tggatcgtcg ttgc                                      34

<210> SEQ ID NO 19
<211> LENGTH: 66
<212> TYPE: DNA
<213> ORGANISM: Artificial Sequence
<220> FEATURE:
<223> OTHER INFORMATION: Synthetic

<400> SEQUENCE: 19
ttcaaaagtt ggagcctttg tacgcctggt tgtgcaagga caggtagttt caatagttac         60
tgttgc                                                                    66

<210> SEQ ID NO 20
<211> LENGTH: 66
<212> TYPE: DNA
<213> ORGANISM: Artificial Sequence
<220> FEATURE:
<223> OTHER INFORMATION: Synthetic

<400> SEQUENCE: 20
ggcaaaagtt ggagcctttg tacgcctggt tgtgcaagga caggtagttt caatagttac         60
tgttgc                                                                    66

<210> SEQ ID NO 21
<211> LENGTH: 66
<212> TYPE: DNA
<213> ORGANISM: Artificial Sequence
<220> FEATURE:
<223> OTHER INFORMATION: Synthetic

<400> SEQUENCE: 21
atcaaaagtt ggagcctttg tacgcctggt tgtgcaagga caggtagttt caatagttac         60
tgttgc                                                                    66

<210> SEQ ID NO 22
<211> LENGTH: 66
<212> TYPE: DNA
<213> ORGANISM: Artificial Sequence
<220> FEATURE:
<223> OTHER INFORMATION: Synthetic

<400> SEQUENCE: 22
ttcaaaagtg caagcctttg tacgcctggt tgtgcaagga caggtagttt caatagttac         60
tgttgc                                                                    66

<210> SEQ ID NO 23
<211> LENGTH: 69
<212> TYPE: DNA
<213> ORGANISM: Artificial Sequence
<220> FEATURE:
<223> OTHER INFORMATION: Synthetic

<400> SEQUENCE: 23
ttcaaaagtt gggcaagcct tgtacgcct ggttgtgcaa ggacaggtag tttcaatagt          60
tactgttgc                                                                 69

<210> SEQ ID NO 24
<211> LENGTH: 63
<212> TYPE: DNA
<213> ORGANISM: Artificial Sequence
<220> FEATURE:
```

<223> OTHER INFORMATION: Synthetic

<400> SEQUENCE: 24
ttcaaaagta gcctttgtac gcctggttgt gcaaggacag gtagtttcaa tagttactgt      60
tgc                                                                    63

<210> SEQ ID NO 25
<211> LENGTH: 66
<212> TYPE: DNA
<213> ORGANISM: Artificial Sequence
<220> FEATURE:
<223> OTHER INFORMATION: Synthetic

<400> SEQUENCE: 25
ttcaaaagtt gggcactttg tacgcctggt tgtgcaagga caggtagttt caatagttac      60
tgttgc                                                                 66

<210> SEQ ID NO 26
<211> LENGTH: 69
<212> TYPE: DNA
<213> ORGANISM: Artificial Sequence
<220> FEATURE:
<223> OTHER INFORMATION: Synthetic

<400> SEQUENCE: 26
ttcaaaagtt ggagcctttg tgcaacgcct ggttgtgcaa ggacaggtag tttcaatagt      60
tactgttgc                                                              69

<210> SEQ ID NO 27
<211> LENGTH: 66
<212> TYPE: DNA
<213> ORGANISM: Artificial Sequence
<220> FEATURE:
<223> OTHER INFORMATION: Synthetic

<400> SEQUENCE: 27
ttcaaaagtt ggagcctttg tacgcctggt tgtgcagaca caggtagttt caatagttac      60
tgttgc                                                                 66

<210> SEQ ID NO 28
<211> LENGTH: 16
<212> TYPE: DNA
<213> ORGANISM: Artificial Sequence
<220> FEATURE:
<223> OTHER INFORMATION: Synthetic

<400> SEQUENCE: 28
gtaaaacgac ggccag                                                      16

<210> SEQ ID NO 29
<211> LENGTH: 33
<212> TYPE: DNA
<213> ORGANISM: Artificial Sequence
<220> FEATURE:
<223> OTHER INFORMATION: Synthetic

<400> SEQUENCE: 29
agaattcagg atgctatcgc tgctttttt gtg                                   33

<210> SEQ ID NO 30
<211> LENGTH: 32
<212> TYPE: DNA
<213> ORGANISM: Artificial Sequence -continued

```
<220> FEATURE:
<223> OTHER INFORMATION: Synthetic

<400> SEQUENCE: 30
agaattcagg aaagttgcca tatggttttg tg                                    32
```

REPLACEMENT THERAPY FOR DENTAL CARIES

PRIORITY

This application claims the benefit of U.S. provisional application 61/603,661, filed Feb. 27, 2012, and U.S. provisional application 61/603,693, filed Feb. 27, 2012, both of which are incorporated herein by reference in their entirety.

BACKGROUND OF THE INVENTION

Dental caries are one of the most prevalent chronic infectious diseases in the world. Over half of U.S. children age 5-9 have at least one cavity or filling; by age 17, nearly 80% of our young people have had a cavity. U.S. Department of Health and Human Services. *Oral Health in America: A Report of the Surgeon General—Executive Summary*. Rockville, Md.: US Department of Health and Human Services, National Institute of Dental and Craniofacial Research, National Institutes of Health, 2000.

Annual expenditures on the treatment of dental caries in the U.S. are estimated to be $40 billion a year according to the Dental, Oral and Craniofacial Data Resource Center. Tooth decay is characterized by the demineralization of enamel and dentin, eventually resulting in the destruction of the teeth. Dietary sugar is often misperceived as the cause of tooth decay; however, the immediate cause of tooth decay is lactic acid produced by microorganisms that metabolize sugar on the surface of the teeth. Studies suggest that of the approximately 700 oral microorganisms, *Streptococcus mutans*, a bacterium found in virtually all humans, is the principal causative agent in the development of tooth decay. Residing within dental plaque on the surface of teeth, *S. mutans* derives energy from carbohydrate metabolism as it converts dietary sugar to lactic acid which, in turn, promotes demineralization in enamel and dentin, eventually resulting in a cavity. The rate at which mineral is lost depends on several factors, including the number of *S. mutans* cells that are present and the frequency and amount of sugar that is consumed.

Therapeutic regimens that take advantage of bacterial interference to replace a pathogenic bacterial strain such as *S. mutans* with a non-pathogenic, effector strain are known as replacement therapies. Successful replacement therapy requires an effector strain that: 1) is non-pathogenic, 2) alters the microenvironment to prevent colonization or outgrowth of a pathogenic organism, and 3) persistently colonizes the host at risk to prevent reinfection by the target pathogenic organism, and aggressively displaces the pathogenic organism from the tissues at risk in the case where the pathogen is part of the host's indigenous flora.

Application of the principles of replacement therapy requires the isolation of a non-cariogenic effector strain of *S. mutans*, e.g., an *S. mutans* strain deficient in lactic acid synthesis that can outcompete native *S. mutans* in the oral cavity of the host. There is a need in the art for stable, lactic acid-deficient, non-cariogenic strains of *S. mutans* that can persistently colonize and aggressively outcompete native *S. mutans* in the oral cavities of the hosts, and that are suitable for use in a replacement therapy in the prevention and/or treatment of dental caries.

The ability of an effector strain to preemptively colonize the human oral cavity and aggressively displace indigenous wild-type strains was initially thought to be a complex phenomenon dependent on a large number of phenotypic properties. However, it was discovered that a single phenotypic property could provide the necessary selective advantage. A naturally occurring strain of *S. mutans* was isolated from a human subject that produces a lantibiotic called MU1140, which is capable of killing virtually all other strains of *mutans streptococci* against which it was tested. See e.g., Hillman et al., Infect. Immun. 44:141 (1984). Mutants were isolated that produced no detectable MU1140 or that produced approximately three-fold elevated amounts. The mutants were used in a rat model to correlate lantibiotic production to colonization potential. It was found that the ability of these strains to preemptively colonize the host and aggressively displace indigenous strains of *S. mutans* increased significantly as the amount of MU1140 produced increased.

The same relationship between MU1140 production and colonization potential was observed in human subjects, where repeated exposures to the wild-type parent strain were required to achieve persistent colonization (Hillman et al. J. Dent. Res. 66:1092 (1985)), whereas a single exposure to the strain producing three-fold elevated amounts of MU1140 was sufficient (Hillman et al. J. Dent. Res. 66:1092 (1987)). The latter strain required over a year to completely replace indigenous strains of *S. mutans* in the mouths of the human subjects. During this period, it is presumed that their susceptibility to dental caries persisted until the levels of indigenous *S. mutans* decreased below a threshold level.

In order to further increase the colonization potential of an effector strain for replacement therapy of dental caries, it is desirable to obtain one or more strains of *S. mutans* that produce elevated amounts of MU1140 or produce variants of this molecule with increased specific activity. Such strains would reduce the period required for the effector strain to eliminate indigenous, lactic acid-producing strains and thereby achieve full effectiveness. Such strains are also more likely to overcome any inherent resistance to colonization, which, while not currently known, may exist in certain individuals in the population being treated. See, e.g., Hillman, *Antonie van Leeuwenhoek* 82: 361-366, 2002.

SUMMARY OF THE INVENTION

In one embodiment the invention provides an isolated recombinant *Streptococcus mutans* strain comprising:

(a) a mutation in a polynucleotide involved in lactic acid synthesis such that expression of lactic acid is diminished by about 80% or more as compared to a wild-type *S. mutans* strain;

(b) a recombinant alcohol dehydrogenase polynucleotide;

(c) a recombinant polynucleotide encoding a lantibiotic comprising Formula I:

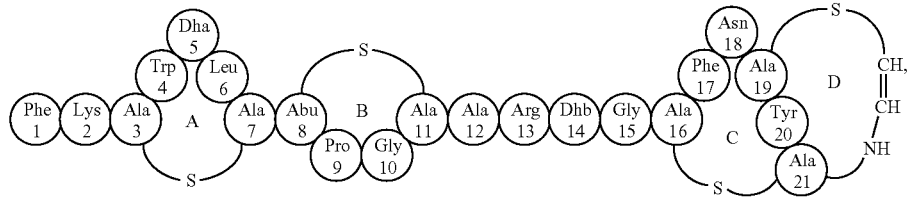

(SEQ ID NO: 1)

wherein the following mutations are present: a Phe1Ile mutation or a Phe1Gly mutation; a Trp4Ala mutation; a Dha5Ala mutation; an Arg13Asp mutation; or combinations of two or more of these mutations. The strain can further comprise a Trp4insAla mutation or a ΔTrp4 mutation. The following amino acid substitutions can also be present: Abu8Ala, or Dhb14Ala, or both Abu8Ala and Dhb14Ala. The strain can further comprise a mutation in a polynucleotide involved in ComE, ComC, or both ComE and ComC synthesis such that expression of ComE, ComC, or both ComE and ComC is diminished by about 80% or more as compared to a wild-type S. mutans strain. The strain can further comprising a mutation in a polynucleotide involved in D-amino acid synthesis such that expression of the D-amino acid is diminished by about 80% or more as compared to a wild-type Streptococcus mutans strain. The polynucleotide involved in D-amino acid synthesis can be dal or a promoter for dal. The recombinant alcohol dehydrogenase polynucleotide can be a Zymomonas mobilis alcohol dehydrogenase polynucleotide or a Streptococcus mutans alcohol dehydrogenase polynucleotide.

Another embodiment of the invention provides a method of reducing the incidence or severity of dental caries in a dental caries-susceptible host comprising administering orally to the host an isolated recombinant S. mutans strain of the invention in an amount effective for replacement of dental caries-causing S. mutans host strains in the oral cavity of the host. The isolated recombinant S. mutans strain can be contained in a mouthwash, toothpaste, chewing gum, floss, chewable tablet, food, or beverage.

Still another embodiment of the invention provides a pharmaceutical composition for reducing the incidence or severity of dental caries comprising an isolated recombinant S. mutans strain of the invention and a pharmaceutically acceptable carrier.

Therefore, the invention provides strains of S. mutans that are stable, lactic acid-deficient, and non-cariogenic that can aggressively outcompete native S. mutans due to, inter alia, the expression of a variant MU1140 lantibiotic that has improved biological activity as compared to a wild-type MU1140 lantibiotic.

BRIEF DESCRIPTION OF THE DRAWINGS

FIG. 2 shows the sequence of chromosomal DNA highlighting mutations of variant MU1140 lanA polynucleotide sequences with the wild type MU1140 lanA polynucleotide sequence.

FIG. 3 shows the primers used for mutagenesis of lanA, the MU1140 structural gene.

FIG. 5 shows the means and standard deviations for the bioactivity of strains producing variants of MU1140 compared to wild-type MU1140.

DETAILED DESCRIPTION OF THE INVENTION

Figure 1A:
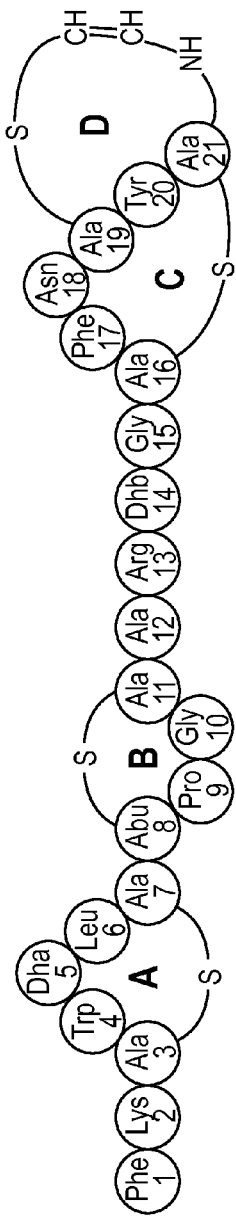
FIG. 1A shows the wild-type MU1140 structure (SEQ ID NO:1).

As used herein, the singular forms "a," "an," and "the" include plural referents unless the context clearly dictates otherwise.

Streptococcus mutans can be recombinantly manipulated to produce no lactic acid or substantially reduced amounts of lactic acid. Hillman et al. J. Appl. Microbiol. 102:1209 (2007). Viable, lactic acid-deficient S. mutans strains can be generated by transforming the strains with nucleic acid encoding a recombinant alcohol dehydrogenase (ADH) such that a recombinant alcohol dehydrogenase is expressed, and introducing a mutation in the lactic acid synthesis pathway to render the recombinant ADH-producing strain lactic acid deficient. The recombinant ADH prevents accumulation of metabolites in the bacterium, thus circumventing any lethality of the lactic acid deficiency. Furthermore, S. mutans strains can be recombinantly engineered to express a variant MU1140 lantibiotic that has greater biological activity than wild-type MU1140 lantibiotics. These strains can outcompete and replace dental caries-causing wild-type, native S. mutans strains in the oral cavity of hosts.

Parent Streptococcus mutans Strains

Any S. mutans strains can be used to construct the recombinant S. mutans strains of the invention. Recombinant S. mutans strains of the invention have a selective advantage over wild-type S. mutans strains that normally colonize the oral cavity. The selective advantage can be conferred by any of a variety of characteristics (e.g., production of an antibacterial compound, reduced or advantageous relative metabolic needs, greater relative growth rate, production of scavengers for metabolites) that promote oral cavity colonization by the strain and replacement of the resident strain colonizing the oral cavity. In one embodiment of the invention, colonization by the recombinant S. mutans strains of the invention will not substantially disrupt colonization by other, non-S. mutans strains (e.g., normal bacterial flora not associated with cariogenesis). For example, infection with a recombinant strain of S. mutans that produces a variant MU1140 lantibiotic with enhanced lantibiotic activity can result in replacement of the resident, cariogenic S. mutans strains without effect upon other resident microbial species of the oral cavity.

Recombinant Streptococcus mutans Strains

A recombinant S. mutans strain is a non-naturally occurring strain of S. mutans that has been generated using any of a variety of recombinant nucleic acid techniques (i.e., techniques involving the manipulation of DNA or RNA). In general, a recombinant S. mutans strain of the invention has a deficiency in lactic acid production; expresses a recombinant alcohol dehydrogenase (ADH) polypeptide; and expresses recombinant polypeptides sufficient to produce a variant MU1140 lantibiotic that has greater biological activity than wild-type MU1140. Recombinant strains of S. mutans can optionally be deficient in ComE, ComC, or both ComE and ComC expression and/or can optionally be auxotrophic for an organic substance not normally present in the oral cavity or diet of a particular host (e.g., a D-amino acid).

Variant MU1140

MU1140 has an overall horseshoe-like shape kinked at the "hinge region" between rings B and C. Smith et al. (2003) Biochem. 42:10372-10384. This shape is the result of a turn-like motif in the hinge region that folds the amino-terminal AB rings (the lipid II binding domain) towards the carboxy-terminal overlapped rings CD. The flexibility of the hinge region is believed to be important in promoting lateral assembly of MU1140, enabling it to abduct and sequester lipid II. The ψ angle of Trp4 and φ angle of Dha5 in ring A help contribute to its flexibility. Also it was determined that the ψ bond of $_S$Ala7 (a residue that is not confined by the thioether ring) rotates 360° allowing ring A to spin freely with respect to ring B. This flexibility is thought to be important in orienting rings A and B during lipid II binding. The hinge region also contains a potentially enzymatically susceptible arginine at residue 13. Mutations in the structural gene (lanA) for MU1140 were generated to determine the effect of the following amino acid alterations: Phe1Ile, Phe1Gly, Trp4Ala, Trp4insAla, ΔTrp4, Dha5Ala, Ala$_S$7 insAla, and Arg13Asp. FIG. 1B.

Figure 6:
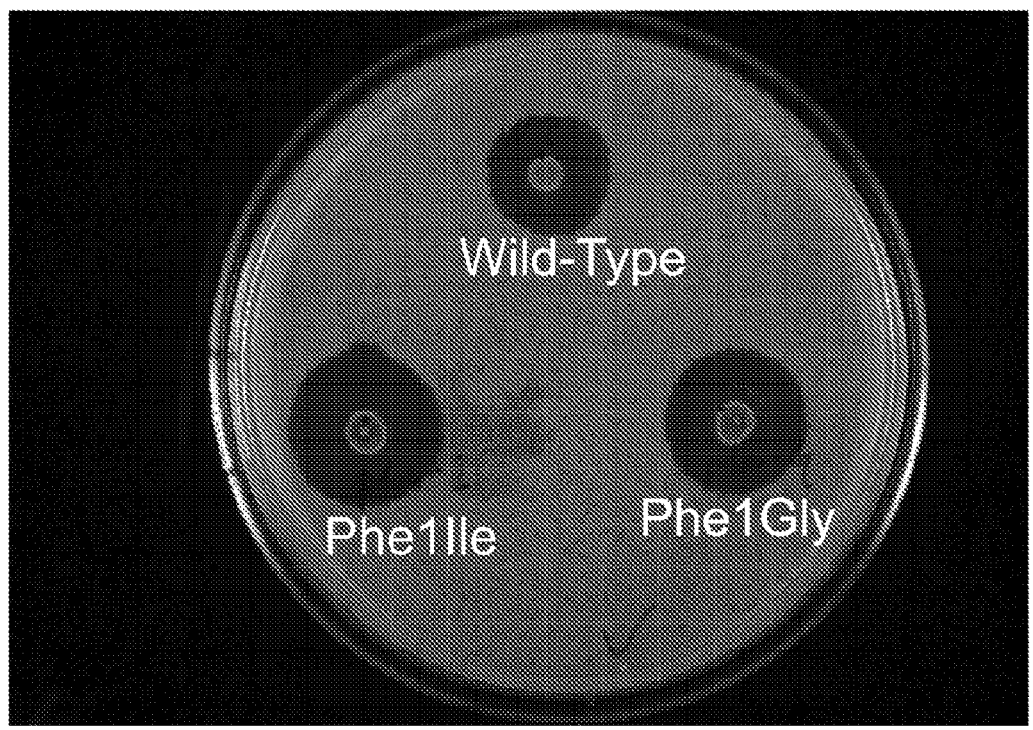
FIG. 6 shows the biological activity of strains producing variants of MU1140 (Phe1Ile and Phe1Gly) compared to wild-type MU1140.

It was found that the variants of MU1140 possessing a deletion of Trp4 or insertion of Ala after Trp4 showed bioactivity activity approximately equivalent to the wild-type in a deferred antagonism assay using *Micrococcus luteus* strain ATCC 272 as the target strain. Wilson-Sanford et al., (2009) Appl. Environ. Microbiol. 75:1381. In this assay, activity is determined by calculating the area of the zone of inhibition. These results indicate that shortening or lengthening ring A had no beneficial or deleterious effect on MU1140 activity, indicating an unexpected permissiveness in the structure of ring A. As shown in FIG. 5, the Trp4Ala substitution resulted in a statistically significant ($p<0.05$) increase in bioactivity when compared to the wild-type. Since both amino acids are uncharged and hydrophobic, it can be speculated that the difference in bioactivity was due to the size difference between the two amino acids. Replacement of Dha5 with Ala also resulted in a statistically significant ($p<0.05$) increase in bioactivity. Insertion of alanine after $_S$Ala at position 7 resulted in a significant ($p<0.05$) reduction of bioactivity. While not wishing to be bound to any particular theory, since it has been determined that $_S$Ala7 freely rotates 360° allowing ring A to spin freely with respect to ring B, it could be concluded that the Ala$_S$7 insAla mutation changed the orientation of the rings during lipid II binding, possibly affecting the affinity of the molecule for its substrate, lipid II. The Arg13Asp substitution showed a very significant ($p<0.05$) increase in bioactivity when compared to the wild-type. While not wishing to be bound to any particular theory, the observed effect may be the result of increased solubility. As shown in FIG. 6, both the Phe1Ile and the Phe1Gly substitutions resulted in statistically significant ($p<0.05$) increases in bioactivity when compared to the wild-type. It is noteworthy that substitution of Arg (AGA/AGG/CGT/CGC/CGA/CGG) with Asp (GAT/GAC) or the substitution of Ala (GCT/GCT/GCA/GCG) for Trp (TGG) or the substitution of Ala (GCT/GCT/GCA/GCG) for Ser (AGT/AGC) or the substitution of Ile (ATT/ATG) or Gly (GGT/GGC/CCA/GGG) for Phe (TTT/TTC) are all very unlikely to occur in nature since they involve multiple point mutations, which may include one or more transversions in the affected codon. While not wishing to be bound to any particular theory, the basis for the increase may be due to increased binding affinity to the lipid II target or to improved efficiency in cleavage of the leader sequence. An effector strain producing a variant MU1140 possessing one or more of these site-directed changes (Phe1Ile, Phe1Gly, Trp4Ala, Dha5Ala, and Arg13Asp) has the potential to be superior to an effector strain producing wild type MU1140 by improving its ability to colonize the oral cavity and aggressively displace disease-causing, indigenous strains of *S. mutans*.

Variants of the lantibiotic MU1140 of the invention are polypeptides comprising post-translational modifications. Post-translational modifications are chemical modifications of a polypeptide after it has been translated. A polypeptide is a polymer of two or more amino acids covalently linked by amide bonds. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

Figure 1B:
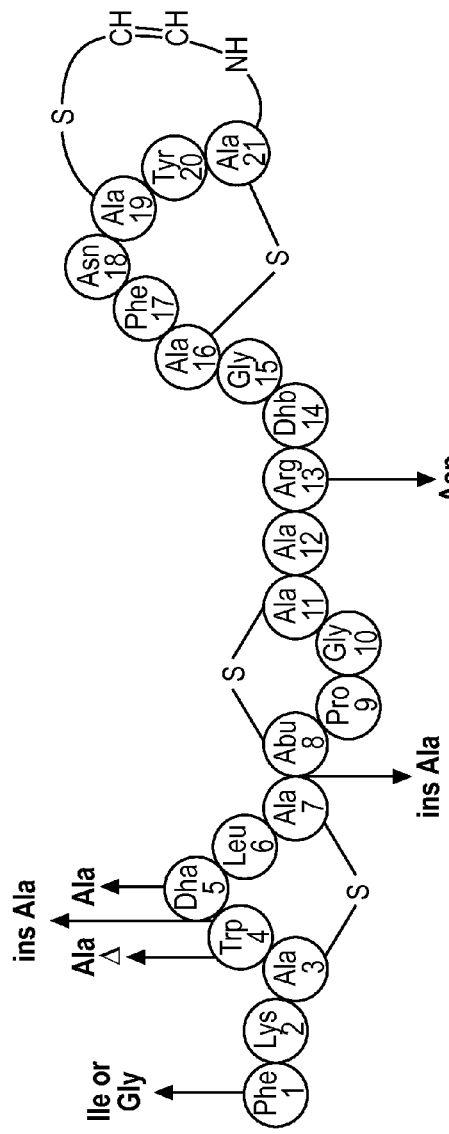
FIG. 1B shows mutation sites of MU1140 (SEQ ID NO:2).

Wild-type MU1140 is shown in FIG. 1A. MU1140 has four rings labeled A, B, C, and D. Two of these rings are formed by lanthionine (Ala-S-Ala) residues, including one in Ring A (Ala$_3$-S-Ala$_7$) and one in Ring C (Ala$_{16}$-S-Ala$_{21}$); there is a methyl-lanthionine residue (Abu-S-Ala) that forms Ring B comprised of the α-aminobutyrate residue in position 8 and the Ala in position 11 (Abu$_8$-S-Ala$_{11}$); and the fourth ring, D, is comprised of the Ala in position 19 linked to an aminovinyl group by a thioether linkage (Ala$_{19}$-S—CH=CH—NH—).

One embodiment of the invention provides one or more of the following variants of the lantibiotic mutacin, MU1140, shown in FIG. 1B (SEQ ID NO:2). That is, the invention includes variants of the wild-type lantibiotic MU1140 (SEQ ID NO:1) with one or more of the following mutations:
1. Phe1Ile or Phe1Gly; that is the phenylalanine at position 1 is changed to isoleucine or glycine.
2. Trp4Ala; that is, the tryptophan at position 4 is changed to alanine.
3. Dha5Ala; that is, the 2,3-didehydroalanine at position 5 is changed to alanine;
4. Arg13Asp; that is, the arginine at position 13 is changed to aspartate.

In one embodiment of the invention a variant of the lantibiotic MU1140 comprises a Phe1Ile or Phe1Gly amino acid substitution; a Trp4Ala amino acid substitution; a Dha5Ala amino acid substitution; an Arg13Asp amino acid substitution; or combinations thereof. An MU1140 variant of the invention can also comprise, e.g., a Trp4insAla in which an alanine is inserted after the fourth tryptophan residue; or a ΔTrp4 in which there is a deletion of the tryptophan at position 4; or both of these changes in the primary amino acid sequence.

Biologically active equivalents of MU1140 lantibiotic polypeptides can have one or more conservative amino acid variations or other minor modifications and retain biological activity. A biologically active equivalent has substantially equivalent function when compared to the corresponding lantibiotic MU1140. In one embodiment of the invention a lantibiotic mutacin has about 1, 2, 3, 4, or 5 or less conservative amino acid substitutions. A conservative substitution is one in which an amino acid is substituted for another amino acid that has similar properties, such that one skilled in the art of peptide chemistry would expect the secondary structure and general nature of the polypeptide to be substantially unchanged. In general, the following groups of amino acids represent conservative changes: (1) ala, pro, gly, glu, asp, gln, asn, dha, abu, dhb, ser, thr; (2) cys, ser, tyr, thr; (3) val, ile, leu, met, ala, gly, dha, abu, dhb, phe; (4) lys, arg, his; and (5) phe, tyr, trp, his. Biologically active equivalent lantibiotic mutacins or other lantibiotic polypeptides can generally be identified by modifying one of the variant lantibiotic mutacin sequences of the invention, and evaluating the properties of the modified lantibiotic mutacin to determine if it is a biological equivalent. A lantibiotic is a biological equivalent if it reacts substantially the same as a lantibiotic mutacin of the invention in an assay such as a zone of inhibition assay, e.g. has 90-110% of the activity of the original lantibiotic mutacin.

Recombinant *S. mutans* strains of the invention comprise a polynucleotide that expresses a functional variant MU1140. Biological activity of a variant MU1140 can be assayed using, e.g., zone of inhibition assays (see Example 2). Recombinant *S. mutans* strains produce enough variant MU1140 to outcompete and substantially eliminate wild-type, cariogenic *S. mutans* from the oral cavity of a host (e.g., reduce the number of wild-type *S. mutans* by about 5, 10, 25, 50, 75, 90, 95, 99, or 100% (or any range between about 5% and about 100%)).

A lantibiotic of the invention can be covalently or non-covalently linked to an amino acid sequence to which the lantibiotic is not normally associated with in nature, i.e., a heterologous amino acid sequence. A heterologous amino acid sequence can be from a non-*Streptococcus mutans* organism, a synthetic sequence, or an *S. mutans* sequence not usually located at the carboxy or amino terminus of a lantibiotic of the invention. Additionally, a lantibiotic of the invention can be covalently or non-covalently linked to compounds or molecules other than amino acids such as indicator reagents. A lantibiotic of the invention can be covalently or non-covalently linked to an amino acid spacer, an amino acid linker, a signal sequence, a stop transfer sequence, TMR stop transfer sequence, a transmembrane domain, a protein purification ligand, or a combination thereof. A polypeptide can also be linked to a moiety (i.e., a functional group that can be a polypeptide or other compound) that facilitates purification (e.g., affinity tags such as a six-histidine tag, trpE, glutathione-S-transferase, maltose binding protein, staphylococcal Protein A or com), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more amino acid residues at, for example, the amino terminus or carboxy terminus of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a lantibiotic of the invention can be part of a fusion protein, which can contain heterologous amino acid sequences. Heterologous amino acid sequences can be present at the C or N terminus of a lantibiotic of the invention to form a fusion protein. More than one lantibiotic of the invention can be present in a fusion protein. Fragments of lantibiotics of the invention can be present in a fusion protein of the invention. A fusion protein of the invention can comprise one or more lantibiotic of the invention, fragments thereof, or combinations thereof.

In one embodiment of the invention, a recombinant *S. mutans* strain of the invention is ATCC 55676 (deposited under the provisions of the Budapest Treaty on the International Recognition of the Deposit of Microorganisms for the Purpose of Patent Procedure and the Regulations thereunder (Budapest Treaty)), which has been genetically engineered to express a variant MU1140 as described herein.

Production of a mutant MU1140 lantibiotic with enhanced biological activity as compared to a wild-type MU1140 lantibiotic can therefore provide an *S. mutans* with a selective advantage over non-MU1140-producing *S. mutans* strains present in the oral cavity of a host. The variant MU1140, when expressed by a recombinant *S. mutans* strain of the invention, eliminates the resident, MU1140-susceptible *S. mutans* strains, thus interfering with colonization of MU1140-susceptible strains and promoting recombinant *S. mutans* colonization of the oral cavity. Since the wild-type, native *S. mutans* is displaced from the oral cavity, the incidence and/or severity of dental caries is reduced.

In one embodiment of the invention the effector strain can additionally express lanB, lanC, lanE, lanF, lanG, lanK, lanM, lanP, lanR, lanT or combinations of two or more of these *S. mutans* polypeptides.

Lactic Acid Expression Deficiency

"Lactic acid deficient" or "deficiency in lactic acid production" means that a recombinant *S. mutans* strain produces substantially decreased amounts of lactic acid relative to wild-type *S. mutans*. Substantially decreased amounts of lactic acid are about 40, 50, 60, 70, 80, 90, 95, or 100% (or any range between about 40% and about 100%) less lactic acid than is produced by a wild-type *S. mutans* strain (e.g. *S. mutans* strain UA159 (ATCC 700610)) or other species belonging to the *mutans streptococcus* group including *Streptococcus sobrinus* (e.g. *S. sobrinus* strain SL1 (ATCC 33478)), *Streptococcus rattus* (e.g., *S. rattus* strain FA1 (ATCC 19645)), *Streptococcus cricetus* (*S. cricetus* strain HS6 (ATCC 19642)), and *Streptococcus ferus* (*S. ferus* strain 8S1)). In one embodiment of the invention, a lactic acid-deficient *S. mutans* effector strain produces no detectable lactic acid. Lactic acid expression can be detected as described in, e.g., Hillman et al., Infect. Immun. 62:60 (1994); Hillman et al., Infect. Immun. 64:4319 (1996); Hillman et al., 1990, Infect. Immun., 58:1290-1295.

Recombinant *S. mutans* strains of the invention can be lactic acid deficient as a result of a non-functional, inactivated, partially functional, or partially inactivated regulatory region, translational signal, transcriptional signal, or structural sequence in the lactic acid synthesis pathway. Regulatory regions, translational signals, and transcriptional signals include, e.g., promoters, enhancers, ribosome binding sites, CAAT box, CCAAT box, Pribnow box, TATA box, etc. Non-functional or inactivated means that the known wild-type function or activity of the polynucleotide, gene, polypeptide or a protein has been eliminated or highly diminished by about 80, 90, 95, or 100% (or any range between about 80% and about 100%) as compared to a wild-type polynucleotide, gene, polypeptide or protein. Partially functional or partially inactivated means that the known wild-type function or activity of the polynucleotide, gene, polypeptide or a protein has been partially diminished by about 20, 30, 40, 50, 60, 70, 79% (or any range between about 20% and about 79%) as compared to a wild-type polynucleotide, gene, polypeptide or protein.

Inactivation or partial inactivation, which renders the polynucleotide, gene, polypeptide, or protein non-functional or partially functional, can be accomplished by methods such as incorporating mutations (e.g., point mutations, frame shift mutations, substitutions, deletions (part of or an entire signal, region or structural polynucleotide), interruptions, and/or insertions) in polynucleotides involved in the lactic acid synthetic pathway. A mutation in a polynucleotide involved in lactic acid synthesis can affect expression of lactic acid such that the expressed amount of lactic acid is diminished by about 20, 30, 40, 50, 60, 70, 80, 90, 95% or more as compared to a wild-type *S. mutans* strain.

For example, inactivation or partial inactivation of lactic acid expression can be effected by inactivating or partially inactivating, e.g., the lactate dehydrogenase (ldh) gene by deleting part of or the entire ldh structural polynucleotide or part of or the entire ldh promoter. Also, inactivation or partial inactivation of lactic acid expression can be effected by inactivating or partially inactivating genes encoding enzymes involved in carbohydrate transport, e.g., the phosphoenolpyruvate phosphotransferase system (pts) gene(s), by deleting part of or the entire pts structural polynucleotide or part of or the entire pts promoter. See e.g., Cvitkovitch et al., J. Bacteriol. 177:5704 (1995). Inactivation or partial inactivation of lactic acid expression can be effected by inactivating or partially inactivating genes encoding enzymes involved in intracellular and extracellular polysaccharide storage, e.g., the glycogen synthase (glgA) gene (see e.g., Spatafora et al., Infect. Immun. 63:2556 (1995)) and the fructosyltransferase (ftf) gene (see e.g., Schroeder et al., Infect. Immun. 57:3560 (1989)), by deleting part of or the entire glgA or ftf structural polynucleotide or part of or the entire glgA or ftf promoter.

One or more defects in the lactic acid synthesis pathway can be introduced by mutagenesis (i.e., exposure of *S. mutans* to a mutagen), selection of spontaneous mutants, or genetic manipulation using recombinant techniques. These techniques are well known in the art (see, e.g., Sambrook et al., 1989, Molecular Cloning: A Laboratory Manual, 2nd Ed., Cold Spring Harbor Laboratory Press, Cold Spring Harbor, N.Y.). In one embodiment of the invention, the lactic acid synthesis pathway defect is introduced using recombinant techniques, e.g., introduction of a defective ldh structural gene into the bacterium and subsequent site-specific recombination to replace the wild-type ldh with the defective ldh. The *S. mutans* ldh gene has been cloned, its nucleotide sequence determined (GenBank accession number M72545), and the recombinant ldh gene expressed in *Escherichia coli* (Hillman et al., 1990, Infect. Immun., 58:1290-1295; Duncan et al., 1991, Infect. Immun., 59:3930-3934). Hillman et al. deleted essentially the entire open reading frame of ldh from a *S. mutans* strain (J. Appl. Microbiol. 102:1209 (2007)).

Alcohol Dehydrogenase Production

Because defects in lactic acid synthesis are lethal for *S. mutans*, the defect in the recombinant, lactic acid-deficient *S. mutans* strains must be complemented by the production of a recombinant alcohol dehydrogenase (ADH). See e.g., Hillman et al., Infect. Immun. 64:4319 (1996). Production of the recombinant ADH prevents accumulation of metabolites, e.g., pyruvate, that otherwise causes the death of lactic acid-deficient *S. mutans*.

An *S. mutans* strain can be genetically engineered to express a recombinant alcohol dehydrogenase for example, alcohol dehydrogenase B, alcohol dehydrogenase II, or iron-containing alcohol dehydrogenase from *Zymomonas mobilis* (see e.g., GenBank Accession No. M15394; Conway et al., 1987, J. Bacteriol., 169:2591-2597), alcohol dehydrogenase from *Streptococcus rattus*, iron-containing alcohol dehydrogenase from *Commensalibacter intestini*, iron-containing alcohol dehydrogenase from *Azotobacter vinelandii*, iron-containing alcohol dehydrogenase from *Enterobacteriaceae bacterium*, alcohol dehydrogenase from *Pseudomonas fluorescens*, iron-containing alcohol dehydrogenase from *Dickeya zeae*, alcohol dehydrogenase from *Proteus mirabilis*, iron-containing alcohol dehydrogenase from *Rhodoferax ferriredcuens*, iron-containing alcohol dehydrogenase from *Rhodospirillum rubrum*, alcohol dehydrogenase from *Pseudomonas brassicacearum*, alcohol dehydrogenase II from *Pseudomonas syringae*, alcohol dehydrogenase from *Dickeya dadantii*, alcohol dehydrogenase from *Citrobacter rodenitium*, iron-containing alcohol dehydrogenase from *Shewanella putrefaciens*, alcohol dehydrogenase from *Vibrio nigripulchritudo*, alcohol dehydrogenase from *Enterobacter aerogenes*, alcohol dehydrogenase from *Pseudomonas savastanoi*, alcohol dehydrogenase from *Salmonella enterica*, iron-containing alcohol dehydrogenase from *Photobacterium leiognathi*, alcohol dehydrogenase from *Photobacterium damselae*, alcohol dehydrogenase from *Xenorhabdus nematophila*, alcohol dehydrogenase from *Xenorhabdus bovienii*, alcohol dehydrogenase II from *Pseudomonas entomophila*, alcohol dehydrogenase II from *Shewanella vilacea*, alcohol dehydrogenase from *Vibrio sinaloensis*, alcohol dehydrogenase from *Shewanella pealeana*, alcohol dehydrogenase from *Vibrio angustum*, alcohol dehydrogenase from *Edwardsiella tarda*, alcohol dehydrogenase from *Salmonella bongori*, iron-containing alcohol dehydrogenase from *Enterobacter asburiae*, alcohol dehydrogenase from *Escherichia coli*, alcohol dehydrogenase 4 from *Vibrio parahaemolyticus*, alcohol dehydrogenase from *Vibrio splendidus*. In one embodiment of the invention, a polynucleotide encoding a bacterial alcohol dehydrogenase or iron-containing alcohol dehydrogenase has at least about 60, 65, 75, 80, 90, 95, 98, 99, or 100% (or any range between about 65% and 100%) homology to *Zymomonas mobilis* alcohol dehydrogenase B.

Additionally, an ADH-encoding polynucleotide can be derived from *S. mutans*, so that introduction of the ADH-encoding polynucleotide, in combination with the native *S. mutans* adh gene, provides for multiples copies of ADH-encoding polynucleotides in the *S. mutans* genome. Alternatively, the recombinant ADH polynucleotide can be generated by introducing a mutation in the regulatory mechanism of the *S. mutans* adh gene to upregulate the production of ADH (e.g., a mutation in the adh promoter to provide increased transcription of the adh gene).

An adh polynucleotide can be introduced into a *S. mutans* strain of the invention using well-known recombinant techniques, for example, transforming the *S. mutans* strain with polynucleotides encoding an ADH polypeptide. Transforming or transformation means that a *S. mutans* has a non-native nucleic acid sequence integrated into its genome or as a plasmid that is maintained through multiple generations. The adh polynucleotide expresses a functional ADH polypeptide such that an *S. mutans* strain of the invention is viable despite the inactivation of lactic acid expression.

Methods for identification, cloning, stable transformation, and expression of polynucleotides encoding, e.g., ADH are routine and well known in the art (see, for example, Sambrook et al., 1989, Molecular Cloning: A Laboratory Manual, 2nd Ed., Cold Spring Harbor Laboratory Press, Cold Spring Harbor, N.Y.). For example, isolation of polynucleotides encoding ADH can be performed by PCR amplification of the molecule from genomic DNA or from a preexisting clone of the gene. Expression of recombinant ADH can be accomplished by operably linking the adh structural polynucleotide to a promoter that facilitates expression in *S. mutans* (e.g., spaP or the native ldh promoter).

Production of a functional ADH can be assayed by, for example, using conventional ADH activity assays (e.g., assays for NAD-dependent oxidation of ethanol) that are well known in the art (Neal et al., 1986, Eur. J. Biochem., 154:119-124). Hillman et al. constructed a strain of *S. mutans* that expressed a functional, recombinant ADH. See e.g., Hillman et al., Infect. Immun. 68:543 (2000).

Auxotrophy

Recombinant *S. mutans* strains of the invention can optionally be genetically engineered to be auxotrophic for an organic substance not normally present in the oral cavity or diet of a host so that the oral cavity colonization by the recombinant *S. mutans* strains can be controlled. That is, the recombinant *S. mutans* strains can optionally be genetically engineered so that they are unable to synthesize a particular organic compound required for growth. For example, the strains of the invention can be auxotrophs for a D-amino acid, such as a D-alanine. Colonization of the auxotrophic strains can then be controlled by regulating the amount of the organic substance in the oral cavity. For example, colonization can be promoted by providing the organic compound periodically to the oral cavity and colonization can be terminated by withholding administration of the organic substance to the oral cavity.

For example, D-alanine is not normally produced or present in the oral cavity or diet of mammals above trace amounts. Therefore, if a recombinant S. mutans of the invention was auxotrophic for D-alanine, then D-alanine would need to be periodically delivered to the oral cavity of the mammal to maintain the colonization of a recombinant S. mutans of the invention in the oral cavity. In the absence of delivery of D-alanine to the oral cavity, the recombinant S. mutans strains of the invention will eventually die out.

In one embodiment of the invention, a recombinant S. mutans is alanine racemase deficient. Alanine racemase is required for D-alanine metabolism. "Alanine racemase deficient" or "deficiency in alanine racemase production" means that a recombinant S. mutans strain produces substantially decreased amounts of alanine racemase relative to wild-type S. mutans. Substantially decreased amounts of alanine racemase are about 40, 50, 60, 70, 80, 90, 95, or 100% (or any range between about 40% and about 100%) less alanine racemase than is produced by a wild-type S. mutans strain. In one embodiment of the invention, an alanine racemase deficient recombinant S. mutans strain produces no detectable alanine racemase. Alanine racemase can be assayed as described in, e.g., Wantanabe et al., J. Biochem. 126:781 (1999).

Inactivation or partial inactivation, which renders the polynucleotide, gene, polypeptide, or protein non-functional or partially functional, can be accomplished by methods such as incorporating mutations (e.g., point mutations, frame shift mutations, substitutions, deletions (part of or an entire signal, region or structural polynucleotide), interruptions, and/or insertions in genes involved in the alanine racemase synthesis. A mutation in a polynucleotide involved in alanine racemase synthesis can effect expression of alanine racemase such that the expressed amount of alanine racemase is diminished by about 20, 30, 40, 50, 60, 70, 80, 90, 95% or more as compared to a wild-type S. mutans strain.

For example, inactivation or partial inactivation of alanine racemase expression can be effected by inactivating or partially inactivating, e.g., the dal gene by deleting part or all of the dal structural polynucleotide or part or the entire dal promoter.

Bacterial auxotrophs can be generated using a variety of techniques well known in the art, such as chemical mutagenesis, selection of spontaneous mutants, and/or recombinant techniques (e.g., transposon mutagenesis, replacement by recombination with a defective or non-functional gene). For example, D-alanine auxotrophic S. mutans strains can be generated by introduction of a defect in the gene encoding alanine racemase (dal), the enzyme that converts L-alanine to D-alanine. Such strains have been generated. See, e.g., Hillman et al., J. Appl. Microbiol. 102: 1209-1219 (2007).

ComE Deficiency

Optionally, a recombinant S. mutans strain of the invention can comprise an inactivated or non-functional comE gene. A strain with an inactivated or non-functional comE gene would be less prone to transformation because ComE is important in the uptake of environmental DNA. Furthermore, comE cannot be complemented.

"ComE deficient" or "deficiency in ComE production" means that a recombinant S. mutans strain produces substantially decreased amounts of ComE protein relative to wild-type S. mutans. Substantially decreased amounts of ComE are about 40, 50, 60, 70, 80, 90, 95, or 100% (or any range between about 40% and about 100%) less ComE protein than is produced by a wild-type S. mutans strain. In one embodiment of the invention, a ComE deficient recombinant S. mutans strain produces no detectable ComE protein. ComE expression can be assayed as described in, e.g., Chen & Gotschlich, J. Bact. 183:3160 (2001).

Recombinant S. mutans strains of the invention can be ComE deficient as a result of a non-functional, inactivated, partially functional, or partially inactivated regulatory region, translational signal, transcriptional signal, or structural sequence in ComE synthesis.

Inactivation or partial inactivation, which renders the polynucleotide, gene, polypeptide, or protein non-functional or partially functional includes methods such as incorporating mutations (e.g., point mutations, frame shift mutations, substitutions, deletions (part of or an entire signal, region or structural polynucleotide), interruptions, and/or insertions) in polynucleotides involved in ComE synthesis. A mutation in a polynucleotide involved in ComE synthesis can effect expression of ComE such that the expressed amount of ComE is diminished by about 20, 30, 40, 50, 60, 70, 80, 90, 95% or more as compared to a wild-type S. mutans strain.

For example, inactivation or partial inactivation of ComE expression can be effected by inactivating or partially inactivating, e.g., the comE gene by deleting part of or the entire comE structural gene or part of or the entire comE promoter. Other genes involved in DNA uptake such as comA, comB, comC, and comD, can also or alternatively be inactivated or partially inactivated.

The defect in ComE synthesis can be introduced by mutagenesis (i.e., exposure of the bacterium to a mutagen), selection of spontaneous mutants, or genetic manipulation using recombinant techniques. A S. mutans strain with a mutated comE gene has been constructed. See, e.g., Hillman et al., J. Appl. Microbiol. 102: 1209-1219 (2007).

Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide.

The polynucleotides of the invention encode the polypeptides of the invention described above (e.g., MU1140 polypeptides, ADH polypeptides, ComE polypeptides, D-amino acid synthesis polypeptides, and lactic acid synthesis polypeptides). In one embodiment of the invention the polynucleotides encode a variant mutacin 1140 polypeptides shown in SEQ ID NOs:20-27, combinations thereof, or fragments thereof. In one embodiment of the invention the effector strain can additionally express lanB, lanC, lanE, lanF, lanG, lanK, lanM, lanP, lanR, lanT or combinations of two or more of these S. mutans polynucleotides.

Polynucleotides of the invention can consist of less than about 600, 500, 400, 300, 200, 100, 66, 60, 50, 45, 30, 15 (or any range between about 600 and 15) contiguous polynucleotides. The purified polynucleotides can comprise additional heterologous nucleotides and/or additional homologous polynucleotides. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A. One embodiment of the invention provides a purified polynucleotide comprising at least about 6, 10, 15, 20, 25, 30, 40, 45, 50, 60, 66, or more contiguous nucleotides of encoding SEQ ID NOs:20-27.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length. Isolated polynucleotides also include non-naturally occurring nucleic acid molecules. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 95, 96, 97, 98, or 99% identical to the polynucleotide sequences of the invention and the complements thereof are also polynucleotides of the invention. Degenerate nucleotide sequences are polynucleotides that encode a polypeptide of the invention or fragments thereof, but differ in nucleic acid sequence from the given polynucleotide sequence due to the degeneracy of the genetic code.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al. (1984) *Nuc. Acids Res.* 12:387), BLASTP, BLASTN, FASTA (Atschul et al. (1990) *J. Molec. Biol.* 215:403), and Besffit program (Wisconsin Sequence Analysis Package, Version 8 for Unix, Genetics Computer Group, University Research Park, 575 Science Drive, Madison, Wis. 53711) which uses the local homology algorithm of Smith and Waterman ((1981) *Adv. App. Math.*, 2:482-489). For example, the computer program ALIGN which employs the FASTA algorithm can be used, with an affine gap search with a gap open penalty of –12 and a gap extension penalty of –2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Polynucleotides of the invention can be isolated from nucleic acid sequences present in, for example, a bacterial sample. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366, 246. A polynucleotide of the invention is operably linked when it is positioned adjacent to or close to one or more expression control elements, which direct transcription and/ or translation of the polynucleotide.

Compositions Comprising Recombinant *S. mutans* of the Invention

Recombinant *S. mutans* strains of the invention can be characterized by: 1) a lactic acid deficiency, and 2) production of a recombinant ADH, 3) variant MU1140 production, 4) optionally, an auxotrophy for a specific organic substance (e.g., a D-amino acid such as D-alanine), 5) optionally, a deficiency in ComE expression, or combinations thereof.

Compositions of the invention can comprise one or more strains of recombinant *S. mutans* strains as described herein and a pharmaceutically acceptable or nutritionally acceptable carrier. The carrier is physiologically compatible with the area of the subject to which it is administered. Carriers can be comprised of solid-based, dry materials for formulation into tablet, capsule, lozenge, or powdered form. A carrier can also be comprised of liquid or gel-based materials for formulations into liquid, gel, and chewing gum forms. The composition of the carrier can be varied so long as it does not interfere significantly with the therapeutic activity of the bacterial strains of the invention.

A composition can be formulated to be suitable for oral administration in a variety of ways, for example in a solid, semi-solid, liquid (including, e.g., a viscous liquid, a paste, a gel, or a solution), a dried mass, a dentifrice, a mouth wash, an oral rinse, a liquid suspension, a beverage, a topical agent, a powdered food supplement, a paste, a gel, a solid food, an oral rinse, a packaged food, a wafer, lozenge, chewing gum and the like. Other formulations will be readily apparent to one skilled in the art. A composition of the invention can include a nutrient supplement component and can include any of a variety of nutritional agents, as are well known, including vitamins, minerals, essential and non-essential amino acids, carbohydrates, lipids, foodstuffs, dietary supplements, and the like.

Compositions of the invention can also include natural or synthetic flavorings and food-quality coloring agents, all of which are compatible with maintaining viability of the bacterial strains of the invention.

A composition of the invention can include one or more gelling agents that can act as an adhesive agent to adhere the composition to the teeth or mouth. The concentration of the gelling agent may be greater than about 2, 4, 6, 8, 10, 15, 20, 30, 40, 50, 60, 70, 80 or less than about 80, 70, 60, 50, 40, 30, or 20 percent by weight of the composition.

Suitable gelling agents and adhesion agents useful in the present invention include, for example, silicone, polyethylene oxide, polyvinyl alcohol, polyalkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaterium-11 (Gafquat 755N), Polyquaterium-39 (Merquat plus 3330), carbomer or carboxypolymethylene (Carbopol), hydroxypropyl methylcellulose, hydroxyethyl cellulose, hydroxypropyl cellulose, corn starch, carboxymethyl cellulose, gelatin and alginate salt such as sodium alginate, natural gums such as gum karaya, xanthan gum, Guar gum, gum arabic, gum tragacanth, and mixtures thereof.

A humectant or plasticizer can be present in compositions of the invention. Humectants or plasticizers include, for example, glycerin, glycerol, sorbitol, polyethylene glycol, propylene glycol, and other edible polyhydric alcohols. The humectants or plasticizers can be present between at about 1% to about 99%, about 10% to about 95%, or at between about 50% and about 80% (or any range between 1% and 99%) by weight of a composition.

Bacteria of the invention can be prepared in, for example, a fermenter. The bacteria can be harvested from the fermenter and can be, for example, concentrated. Bacteria of the invention can be prepared for use by, for example, dehydration, air drying, lyophilizing, freezing, and spray-drying. Bacteria can also be prepared for use by microencapsulation (see e.g., U.S. Pat. No. 6,251,478) or by coating with a protective substance such as, for example, lipid material such as triacylglycerols, waxes, organic esters, soybean oil, cottonseed oil, palm kernel oil, and esters of long-chain fatty acids and alcohols. In one embodiment of the invention the coated or encapsulated bacteria of the invention are released in the oral cavity of the host.

Methods of Treatment and Prevention of Cavities

The recombinant *S. mutans* of the invention can be present in a composition of the invention in a therapeutically effective amount. Therapeutically effective means effective to prevent or reduce the number or incidence (e.g., 5, 10, 20, 30, 40, 50, 60, 70, 80, 90 or 100% fewer cavities than controls that did not receive the composition) and/or reduce the severity (e.g., 5, 10, 20, 30, 40, 50, 60, 70, 80, 90 or 100% less severe cavities than controls that did not receive the composition) of cavities.

A therapeutically effective amount or dosage is an amount or dosage of a composition of the invention at high enough levels to prevent caries and/or reduce caries number and/or caries severity, but low enough to avoid serious side effects (at a reasonable benefit/risk ratio), within the scope of sound medical/dental judgment. The therapeutically effective amount or dosage of a composition of the invention may vary with the particular condition being treated, the age and physical condition of the patient being treated, the severity of the condition, the duration of treatment, the nature of concurrent therapy, the specific form of the source employed, and the particular vehicle from which the composition is applied.

The compositions of the invention can be applied in a therapeutically effective amount to the oral cavity of a host for the treatment and/or prevention of cavities. A composition of the invention may be swallowed or may be rinsed around the oral cavity and then spit out, such that it is not substantially delivered to the gastrointestinal tract. That is, less than about 10, 5, 4, 3, 2, or 1, 0.5, or 0.1% (or any range or value between about 10 and 0.1%) of the delivered bacteria are delivered to the gastrointestinal tract. Treatment means inducing a reduction in the amount or intensity (or combination thereof) of cavities.

Prevention means that substantially no dental caries occur after exposure of the host to one or more recombinant *S. mutans* strains of the invention either permanently (as long as the bacteria of the invention remain in sufficient numbers in the subject's oral cavity), or temporarily (e.g., for about 1, 2, 3, 4, 5, 6 or more months). The bacterial strains of the invention can form at least a part of the transient or indigenous flora of the oral cavity and exhibit beneficial prophylactic and/or therapeutic effects.

Treatment means reducing the amount of wild-type *S. mutans* in the oral cavity of a host such that remineralization of small carious lesions can occur and that further damage to larger carious lesions is stopped or slowed. The amount of wild-type *S. mutans* in the oral cavity can be reduced by about 20, 30, 40, 50, 60, 70, 80, 90, or 100% (or any range between about 10 and 100%).

In one embodiment of the invention prevention means prevention in a population of subjects. That is, given a population of subjects, the treatment can prevent dental caries in about 5, 10, 20, 30, 40, 50, 60, 70, 80, 90% or more of the subjects as compared to a control population that did not receive the treatment.

In one embodiment of the invention a composition can comprise one or more isolated recombinant strains of the invention along with one or more isolated *Streptococcus oralis* strains and/or one or more isolated *Streptococcus uberis* strains.

*Streptococcus oralis* (previously known as *Streptococcus sanguis* Type II) and *S. uberis* are important components in maintaining the normal, healthy balance of microorganisms that compose the periodontal flora. See, Socransky et al., *Oral Microbiol. Immunol.* 3:1-7 (1988); Hillman and Shivers, *Arch. Oral. Biol.,* 33:395-401 (1988); Hillman, et al., *Arch. Oral. Biol.,* 30:791-795 (1985). *S. oralis* produces hydrogen peroxide, which can inhibit periodontal pathogens such as *Actinobacillus actinomycetemcomitans* (Aa), *Bacteroides forsythus*, and *P. intermedia*. Therefore, *S. oralis* and *S. uberis* can be useful in the maintenance of oral health. Compositions of the invention can comprise one or more isolated strains of *S. oralis*, for example, ATCC 35037, ATCC 55229, ATCC 700233, ATCC 700234 and ATCC 9811. Other strains of *S. oralis* include KJ3 and KJ3sm. KJ3sm is a naturally occurring genetic variant of KJ3 that is resistant to streptomycin. The streptomycin resistance is advantageous because it provides a marker for easy isolation of the bacteria. Additionally, streptomycin resistant strains are slightly attenuated and do not survive as long in an oral cavity as wild-type strains. This property is useful where the goal is to non-persistently colonize the oral cavity of an animal with the bacteria.

*S. uberis* in plaque has been found to correlate with periodontal health, in particular by interfering with the colonization by periodontal pathogens such as *Porphyromonas gingivalis, Campylocbacter recta*, and *Eikenella corrodens*. Compositions of the invention can comprise one or more isolated strains of *S. uberis*, for example, ATCC 13386, ATCC 13387, ATCC 19435, ATCC 27958, ATCC 35648, ATCC 700407, ATCC 9927, strain KJ2 or strain KJ2sm. KJ2sm is a naturally occurring genetic variant of KJ2. That is streptomycin resistant and provides the same advantages as for streptomycin-resistant strains of *S. oralis*. One or more isolated strains of *S. oralis* or one or more isolated strains of *S. uberis*, or both, can be used in compositions and methods of the invention. Additional oral care benefits of these compositions of the invention include, for example, the treatment and/or prevention of periodontitis, oral bacterial infections and diseases, oral wounds, *Candida* or fungal overgrowth, halitosis, or xerostomia-induced dental caries and associated periodontal diseases, the promotion of wound healing, teeth whitening or a combination thereof to a subject.

One embodiment of the invention provides a method for treating dental caries comprising administering a composition comprising one or more recombinant *S. mutans* strains of the invention to the oral cavity of a subject in need thereof. That is, the subject has one or more dental caries.

One embodiment of the invention provides for the prevention of dental caries in normal, healthy subjects. Another embodiment of the invention provides for treatment and/or prevention of dental caries in subjects having an increased susceptibility to dental caries as compared to normal, healthy subjects. In both embodiments, the method consists of administering a composition comprising one or more recombinant *S. mutans* strains to the oral cavity of a subject.

Subjects have an increased susceptibility to dental caries when they are more likely than a normal, healthy host to develop dental caries. Such hosts may have, for example, decreased saliva production (e.g., patients undergoing radiation therapy on the head or neck, patients having Sjögren's syndrome, diabetes mellitus, gastro-esophageal reflux disease, diabetes insipidus, or sarcoidosis, patients taking antihistamines and antidepressants or other medications that cause "dry mouth"), smokers, smokeless tobacco users, patients having a genetic predisposition (Shuler, J. Dent. Ed. 65:1038 (2001)), or are infants (0 to 2 years old or 6 months to 2 years old), children (3 years to 18 years old), or elderly (older than 65).

The invention also provides a method of reducing the amount in a subject of bacteria that can cause dental caries. The method comprises administering a composition comprising one or more recombinant *S. mutans* strains of the invention to the oral cavity of a subject having one or more strains or species of bacteria that can cause dental caries. The compositions can be administered just once or on a regular basis. The number of the one or more strains or species of bacteria that can cause dental caries in the subject is reduced. The reduction can be about a 5, 10, 25, 50, 75, 90, 95, 99, or 100% (or any range between about 5% and about 100%) reduction in numbers.

Optionally, prior to the administration of the composition of the invention, one or more bacteria that can cause dental caries can be detected and/or quantitated using any detection/quantitation method known in the art. Those of skill in the art are aware of methods of detection of bacteria that cause dental caries. Optionally, prior to the administration of the composition of the invention, one or more dental caries can be diagnosed in the subject using any methodology known in the art.

Another embodiment of the invention provides a method of preventing dental caries in a subject. The method comprises obtaining data regarding a therapeutically effective dosage range for prevention of dental caries in a particular type of subject and determining the effective dosage range of recombinant *S. mutans* for the particular type of subject. A particular type of subject can be, for example, a subject with decreased saliva production (e.g., patients undergoing radiation therapy on the head or neck, patients having Sjögren's syndrome, diabetes mellitus, gastro-esophageal reflux disease, diabetes insipidus, or sarcoidosis, patients taking antihistamines and antidepressants or other medications that cause "dry mouth"), smokers, smokeless tobacco users, patients having a genetic predisposition, or are infants (0 to 2 years old or 6 months to 2 years old), children (3 years to 18 years old), or elderly (older than 65). The determined therapeutically effective dosage range for the particular type of subject of one or more recombinant *S. mutans* strains of the invention are administered to the oral cavity of the particular type of subject.

Compositions can be administered to the oral cavity of a host or subject such as an animal, including a mammal, for example, a human, a non-human primate, a dog, a cat, a horse, a bovine, a goat, or a rabbit.

The compositions of the invention can be orally administered in for example, food, water, a dentifrice, a gel, a paste, an emulsion, aerosol spray, chewing gum, lozenge, tablet, capsule, or a liquid suspension. The bacteria can either be already formulated into food, water, gel or other carrier or can be a composition (e.g., powder, tablet or capsule) that is added to the carrier (e.g., food, water, dentifrice, gel, paste, emulsion, aerosol spray, or liquid suspension) by the user prior to consumption.

One embodiment of the invention provides a method of non-persistently colonizing an oral cavity of a subject with therapeutically-effective bacteria comprising administering to the oral cavity of a subject a composition of the invention. In one embodiment of the invention the administered bacterial strains do not permanently colonize the oral cavity, rather the strains are present in the oral cavity for about 1 day, about 1 week, about 2 weeks, about 3 weeks, about 1 month, about 3 months or about 12 months after administration of the bacteria.

In another embodiment of the invention, recombinant strains of *S. mutans* persistently colonize an oral cavity of a host for a long term period, e.g., 2 weeks, 1 month, 3 months, 6 months, 1 year, 5 years, or more or for the life of the host.

Compositions of the invention can be administered at a dose of about $1 \times 10^3$, $1 \times 10^5$, $1 \times 10^7$, $1 \times 10^8$, $1 \times 10^9$, or $1 \times 10^{11}$ CFU (or any range or value between about $1 \times 10^3$ and about $1 \times 10^{11}$) of viable bacteria. A dose of a composition of the invention can be administered at four times a day, three times a day, twice a day, once a day, every other day, two times a week, weekly, biweekly, monthly, or yearly. One, two, or more doses of a composition of the invention can be administered per day for about 1 day, about 1 week, about 2 weeks, about 1 month, about 2 months, about 3 months, about a year or more. In one embodiment of the invention, a composition of the invention is administered one time and is effective for a long term period.

A composition of the invention can comprise bacterial strains at a concentration between about 0.01% and about 50%, or about 0.1% to about 25%, or about 1.0% to about 10% or any ranges or values in between 0.01% and 50% by weight of the composition.

A kit of the invention can contain a single dose, a one week, one month, two month, three month, four month, five month, six month, or 12 month supply of a composition of the invention. A composition of the invention can be packaged and, in turn, a plurality of the packaged compositions can be provided in a storage container or outer package or carton. Where the one or more strains of *S. mutans* are auxotrophic, the kit can include a bacterial auxotroph-maintaining amount of an organic substance, e.g., a composition comprising a D-amino acid such as D-alanine.

Where a composition of the invention comprises one or more strains of *S. mutans* that are auxotrophic for an organic substance, a bacterial auxotroph-maintaining amount of an organic substance can be administered to hosts to maintain the recombinant *S. mutans* in the oral cavity. A "bacterial auxotroph-maintaining amount" is an amount of an organic substance sufficient to maintain viability of the recombinant *S. mutans* auxotroph in the oral cavity. For example, where the recombinant *S. mutans* is auxotrophic for D-alanine, a D-alanine bacterial auxotroph-maintaining amount is an amount of D-alanine sufficient for survival of the D-alanine auxotrophic strain in the host's oral cavity. In general, a single dose of a D-alanine bacterial auxotroph-maintaining amount of D-alanine contains about 1, 5, 10, 20, 25, 50, 75 or 100 mg (or any range between about 1 and about 100 mg). The concentration of D-alanine in a composition in the form of a solution is about 0.01, 1, 10, 25, 50, 75, 100, or 167 mg/ml (the latter being a saturated solution of D-alanine in water at 25° C.) (or any range between about 0.01 and about 167 mg/ml). The concentrations of D-alanine in a composition can vary according to the carrier used and the saturation point of D-alanine in that specific carrier.

The organic substance, e.g., D-alanine, required for maintenance of the auxotrophic, recombinant *S. mutans* in the oral cavity can be formulated as a mouthwash, chewing gum, dental floss, toothpaste, chewable tablet, food, beverage or any other formulation suitable for oral administration to the host's oral cavity. In addition to the organic substance (e.g., D-alanine), the composition can additionally contain flavoring agents, coloring agents, fragrances, or other compounds that increase the palatability of the composition and/or enhance patient compliance without compromising the effectiveness of the organic substance contained in the composition.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Mutagenesis of MU1140

The *Streptococcus mutans* genome database and lan gene cluster, GenBank/EMBL accession number (AF051560), was used to design primers for the mutagenesis and sequencing work. The open reading frame (ORF) of the native MU1140 structural gene (lanA) plus 500 base pairs (bp) of 5" and 3' flanking DNA was cloned into the pVA891 plasmid to create p190. The cloned insert in p190 was derived by PCR amplification of chromosomal DNA of *S. mutans* strain JH1140 (ATCC 55676) using the primer sequences of SRWlanA_1 and SRWlanA_2 (see FIG. 3). Reagents and media were purchased from Fisher Scientific, and enzymes were purchased from New England BioLabs (Ipswich, Mass.).

Polymerase Chain Reaction (PCR)

Mutations (see FIG. 1B) were introduced into the propeptide region of lanA, the structural gene for MU1140, to create the variants of MU1140. See FIG. 2. The p190 plasmid (J. D. Hillman, unpublished) was used as a template and the site specific mutations were introduced using two-step PCR. In the first step, the upstream and downstream outside primers (SRWlanA_1 and SRWlanA_2) were paired with appropriate inside primers (e.g., SRWlanA_1/Trp4Ala_2 and SRWlanA_2/Trp4Ala_1) (FIG. 3), one of which was synthesized to contain an altered base sequence relative to the wild type sequence. The result of this step was the production of two fragments, one that included 5' flanking DNA and a portion of lanA, including the site directed base alterations. The second fragment contained the remainder of lanA plus 3' flanking DNA. Primers used to produce the MU1140 variants are found in FIG. 3. The two fragments were then mixed in equal amounts and subjected to a second round of PCR using the two outside primers, SRWlanA_1 and SRWlanA_2, to yield the final amplicon.

PCR reactions were performed using Taq polymerase in a final volume of 50 μL containing 0.4 μmol of each primer, 50 ng of template DNA, 0.016 mMdNTP, and 1 unit of DNA polymerase in 1× polymerase buffer. Amplification conditions for each fragment were as follows: preheat at 95° C. for 1 min, followed by 27 cycles incubation with denaturation (95° C.) for 30 sec, annealing (56° C.) for 30 sec and extension (72° C.) for 2 min followed by a final extension (72° C.) for 10 min. Both fragments were combined 50:50 and amplified using the two outside primers SRWlanA_1 and SRWlanA_2 under the same amplification conditions as mentioned above.

The final PCR product was ligated into a TOPO-TA vector (Invitrogen, Carlsbad, Calif.) following kit directions and transformed into DH5α-T1® cells (Invitrogen) using standard methods and spread on LB plates containing 50 μg/mL of ampicillin and 40 μL of X-gal (40 mg/mL). Blue-white screening was utilized to identify colonies containing an insert. Plasmid DNA from each colony was purified using a PureYield Plasmid Miniprep System (Promega, Madison, Wis.) according to the manufacturer's instructions. Purified plasmid was subjected to restriction digest using EcoRI and examined by agarose gel electrophoresis to identify those that have a cloned insert of proper size (~1100 bp). Plasmids containing the proper sized insert were sequenced using M13 Forward (−20) primer, 5'-GTAAAACGACGGCCAG-3' (SEQ ID NO:28), to confirm the proper insertion, deletion, or replacement of nucleotide bases.

Recombination

Restriction enzyme digestion was performed on purified plasmid from colonies harboring a confirmed mutation. The insert were separated from the TOPO plasmid by electrophoresis, excised from the gel, and purified using a Qiagen Gel Extraction Kit (Qiagen, Valencia, Calif.). The purified insert was then ligated into the *S. mutans* suicide vector, pVA891, in a 3:1 insert:vector ratio using T4 DNA ligase at 16° C. overnight. The resultant plasmid was then transformed into DH5α cells using standard methods and spread on LB plates containing 300 μg/mL of erythromycin. Colonies which arose following incubation were analyzed to verify proper insert size and sequence as described above.

Purified pVA891 DNA containing confirmed inserts was transformed into *S. mutans* strain JH1140 (ATCC 55676) as follows: *S. mutans* was grown overnight then diluted 1:15 in fresh THyex broth (30 g/L THB, 3 g/L yeast extract), 200 μL of diluted cells were added to a 96 well plate and incubated at 37° C. for 2 hours. Two microliters of competence stimulating peptide (CSP, 0.1 μg/mL; see e.g., Li et al., J. Bacteriol. 183:897 (2001)) was added, and plates were incubated for an additional 6 hours. See Li et al., (2002) J. Bacteriol. 184:2699. Fifty microliters of cells were then plated onto pre-warmed THyex agar plates (30 g/L THB, 3 g/L yeast extract, and 15 g/L of nutrient agar) containing 300 μg/mL of erythromycin and incubated at 37° C. for 48 hours. Genomic DNA was extracted from clones that arose utilizing a standard chloroform/phenol extraction method and the DNA was used as template for PCR that used SRWlanA_1 and SRWlanA_2 to identify heterodiploid clones presumed to have one wild type and one mutated copy of the lanA gene separated by vector DNA, as previously described by Hillman et al., (2000) Infect. Immun. 68:543-549.

Confirming Genetic Identity of Mutant Constructs

Clones containing the desired lanA mutations were obtained by spontaneous resolution of the heterodiploid state as follows: several confirmed heterodiploids were grown overnight in 20 mL THyex broth that did not contain erythromycin. The cultures were subcultured (1:20 dilution into fresh media) and again grown overnight to saturation. The cultures were then diluted 100,000 fold and spread onto large THyex agar plates and incubated at 37° C. for 48 hours. Resultant colonies were replica patched onto medium with and without erythromycin to identify spontaneous recombinants in which elimination of the pVA891 plasmid (expressing the erythromycin resistance gene) and either the wild-type or mutated lanA gene had occurred. Erythromycin sensitive colonies that were identified from the replica plating technique were re-tested on medium with and without erythromycin. The lanA region of erythromycin sensitive clones was amplified by PCR as described above. The amplicons generated were sequenced to identify clones possessing only the modified lanA genes. BLAST sequence analysis was used to compare the wild-type sequence of lanA to the lanA of suspected mutants (FIG. 2). The mutants generated were: Trp4Ala, Trp4insAla, ΔTrp4, Dha5Ala, Ala$_s$7 insAla, and Arg13Asp.

Example 2

Bioactivity of Mutants

The parent *S. mutans* strain, JH1140 (ATCC 55676), and the mutants were grown to an $OD_{600}$ of 0.8 and diluted to an $OD_{600}$ of 0.2. Samples (2 μL) of the cultures were spotted in triplicate on a pre-warmed THyex agar plate (150×15 mm) and allowed to air dry. This assay was performed in this manner to help ensure that each sample had the same colony size for comparing zones of inhibition. The plate was incubated for 24 hours at 37° C., and then placed in an oven at 55° C. for thirty minutes to kill the bacteria before the *M. luteus* ATCC 272 indicator strain was overlayed in molten top agar. Heat killing the bacteria prevented any further antimicrobial compound production. *M. luteus* ATCC 272 was grown to an $OD_{600\ nm}$ between 0.4 and 0.8 and diluted to an $OD_{600\ nm}$ of 0.2. Then, 400 μl of these cells was added to 10 ml of molten top agar (42° C.) (30 g/L Todd Hewitt Broth and 7.5 g/L Nutrient agar). All 10 mL of top agar containing the standardized suspension was added to each plate containing approximately 50 mL of THyex agar. The plates were allowed to solidify before being inverted and incubated overnight at 37° C. Each inhibitory zone radius was measured in mm from one edge of the colony to the farthest portion of the zone. The area of the inhibitory zone was calculated for each zone and compared to the average zone area of the wild-type (n=10).

Figure 4B:
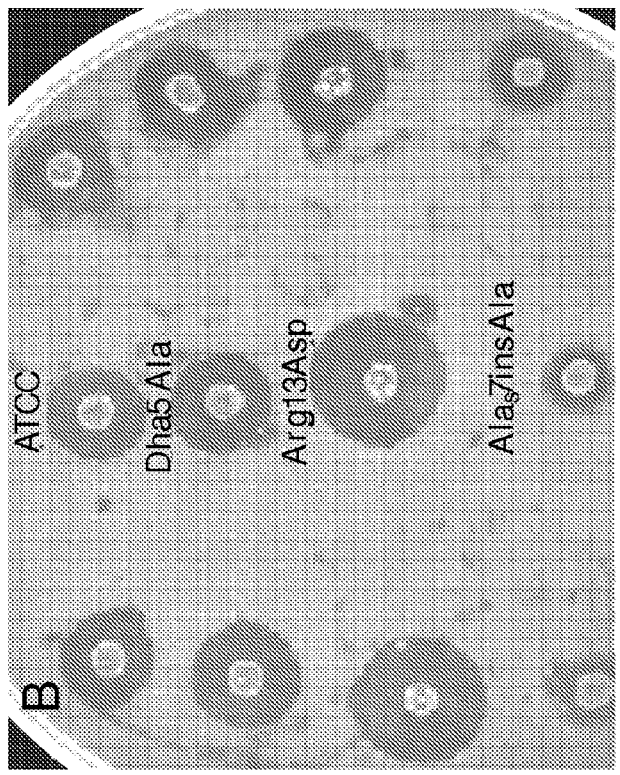
FIG. 4A-B shows the results of the zone of inhibition plate assays.
Figure 4A:
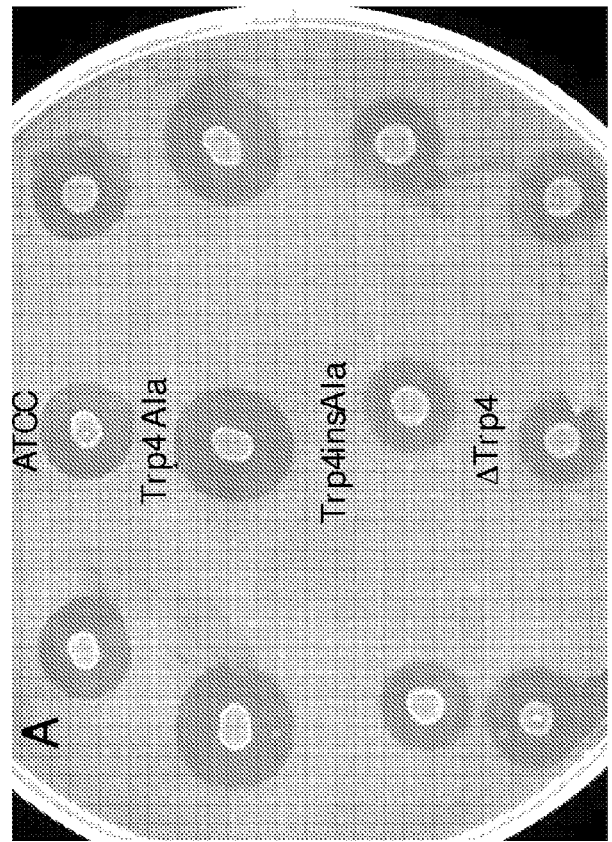

FIG. 4 illustrates the bioactivity of strains producing variants of MU1140 compared to wild-type MU1140. The results are summarized in FIG. 5, which shows that the strains producing Trp4insAla and ΔTrp4 had zones that were not significantly different (Student's t test, p>0.05) than the wild-type. The strain producing Arg13Asp had the largest inhibitory zone area amounting to a 2.57-fold increase relative to wild-type (p<0.001). The strains producing Trp4Ala and Dha5Ala produced significant (p<0.001) 2.12-fold and 1.87-fold increases, respectively, relative to the wild-type. The strain producing Ala$_s$7 insAla had the smallest zone area, which amounted to a significant (p<0.001) 2-fold reduction in zone area when compared to the wild-type. FIG. 6 shows the biological activity of strains producing other variants of MU1140 (Phe1Ile and Phe1Gly) compared to wild-type MU1140. The strains producing Phe1Ile and Phe1Gly demonstrated significant (p<0.001) 1.82-fold and 1.57-fold increases, respectively, relative to the wild-type.

There has been a number of studies that used site directed mutagenesis of the structural gene for nisin and certain other lantibiotics (reviewed by Chatterjee et al. (2005) Chem. Rev. 105:633) to analyze the importance of particular amino acids in the activity of these molecules. Rarely have these mutations resulted in increased bioactivity.

The most interesting result was obtained for the Arg13Asp mutant. This mutation resulted in an unexpected, highly significant increase in bioactivity when compared to the wild-type. Here there was replacement of a positively charged residue with a negatively charged residue in the hinge region. This finding is contrary to the conventional belief that negative charges for lantibiotics should reduce bioactivity since positive charges are thought to aid in the interaction of the antibiotic with negatively charged lipids present in the target cell membrane. This mutation also removed a trypsin cleavable site from the compound, thereby making it more stable to enzymatic hydrolysis. Furthermore, the Trp4Ala, Dha5Ala, and Arg13Asp are transversion mutations that would likely not naturally occur.

The mutations to MU1140 described herein are therefore unexpected and unpredictable in view of the prior art and result in variant MU1140 molecules that have vastly improved biological and structural characteristics as compared to wild-type MU1140. Mutations that increase activity are important from the standpoint of improving the colonization potential of an *S. mutans* effector strain. The ability of *S. mutans* strains to colonize the oral cavity of rodents and humans has been previously shown to correlate with the amount and/or activity of MU1140 produced. In addition, the ability of *S. mutans* strains to aggressively displace indigenous strains of *S. mutans* in the oral cavity of rodents and humans has been previously shown to correlate with the amount and/or activity of MU1140 produced. See e.g., Hillman et al., Infect. Immun. 44:141 (1984); Hillman et al., J. Dent. Res. 66:1092 (1987). Therefore, an *S. mutans* effector strain of the invention that expresses a variant MU1140 as described herein will have unexpected and improved characteristics as compared to effector *S. mutans* strains that do not express a variant MU1140 of the invention. That is, *S. mutans* effector strains expressing a variant MU1140 will have improved ability to colonize and aggressively outcompete and replace native *S. mutans* in the oral cavities of the hosts relative to *S. mutans* effector strains that do not express a variant MU1140 as described herein.

Example 3

Minimum Inhibitory Concentration

Wild-type mutacin 1140, mutacin 1140 with a F1I mutation, mutacin 1140 with a W4A mutation, and mutacin 1140 with a R13D mutation was purified to about 90% purity (measured via HPLC). The minimum inhibitory concentration (MIC) of MU1140 and variants of MU1140 was determined against several bacteria. The MIC is the lowest concentration of MU1140 that will inhibit the visible growth of a microorganism after 24 hour incubation. A lower MIC is an indication of greater inhibitory activity. Preparation of the antimicrobial agent and bacterial inoculum for minimum inhibitory concentrations (MICs) was performed by following the method described in Clinical Laboratory Standard Institute (CLSI) M07-8A with some minor modifications. *Streptococcus mutans* UA159 was tested overnight in a shaking incubator to maintain uniform dispersion of the bacteria. *Clostridium difficile* UK1 was tested in an anaerobic chamber at 37° C. The medium used was THyex. The results are shown in Table 1.

TABLE 1

| MU1140 Variant | *Streptococcus mutans* UA159 | *Streptococcus pneumonia* FA1 | *Staphylococcus aureus* FA1 | *Micrococcus luteus* ATCC10240 | *Clostridium difficile* UK1 |
|---|---|---|---|---|---|
| Mu1140 Wild-type | 2 | 0.5 | 16 | 0.0625 | 16 |
| Mu1140 F1I | 2 | 0.25 | 8 | 0.0156 | 8 |
| Mu1140W4A | 2 | 0.125 | 16 | 0.0312 | 8 |
| Mu1140R13D | 2 | 4 | >16 | 0.125 | 16 |

While the MIC is not necessarily lower for each organism for each mutant, each mutant may still have advantages over the wild-type MU1140 because it may, for example, be easier to produce, easier to transport, have better shelf stability, have better serum stability, or have better proteolytic stability, among other advantageous properties.

What is claimed is:

1. An isolated recombinant *Streptococcus mutans* strain comprising:
   (a) a mutation in a polynucleotide involved in lactic acid synthesis such that expression of lactic acid is diminished by about 80% or more as compared to a wild-type *S. mutans* strain;
   (b) a recombinant alcohol dehydrogenase polynucleotide; and
   (c) a recombinant polynucleotide encoding a lantibiotic comprising Formula I:

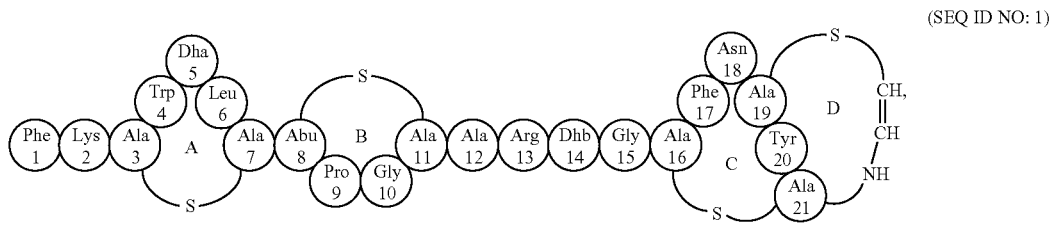

(SEQ ID NO: 1)

wherein the following mutations are present: a Phe1Ile mutation or a Phe1Gly mutation; a Trp4Ala mutation; a Dha5Ala mutation; an Arg13Asp mutation; or combinations of two or more of these mutations.

2. The isolated recombinant *Streptococcus mutans* strain of claim 1, wherein the lantibiotic comprising Formula I further comprises a Trp4insAla mutation or a ΔTrp4 mutation.

3. The isolated recombinant *Streptococcus mutans* strain of claim 1, wherein the lantibiotic comprising Formula I further comprises the following amino acid substitutions: Abu8Ala, or Dhb14Ala, or both Abu8Ala and Dhb14Ala.

4. The isolated recombinant *Streptococcus mutans* strain of claim 1, further comprising a mutation in a polynucleotide involved in ComE, ComC or both ComE and ComC synthesis such that expression of ComE, ComC, or both ComE and ComC is diminished by about 80% or more as compared to a wild-type *S. mutans* strain.

5. The isolated recombinant *Streptococcus mutans* strain of claim 1, further comprising a mutation in a polynucleotide involved in D-amino acid synthesis such that expression of the D-amino acid is diminished by about 80% or more as compared to a wild-type *Streptococcus mutans* strain.

6. The isolated recombinant *Streptococcus mutans* strain of claim 5, wherein the polynucleotide involved in D-amino acid synthesis is dal or a promoter for dal.

7. The isolated recombinant *Streptococcus mutans* strain of claim 1, wherein the recombinant alcohol dehydrogenase polynucleotide is a *Zymomonas mobilis* alcohol dehydrogenase polynucleotide or a *Streptococcus mutans* alcohol dehydrogenase polynucleotide.

8. A method of reducing the incidence or severity of dental caries in a dental caries-susceptible host comprising administering orally to the host the isolated recombinant *Streptococcus mutans* strain of claim 1 in an amount effective for replacement of dental caries-causing *Streptococcus mutans* host strains in the oral cavity of the host.

9. The method of claim 8, wherein the isolated recombinant *Streptococcus mutans* strain is contained in a mouthwash, toothpaste, chewing gum, floss, chewable tablet, food, or beverage.

10. A pharmaceutical composition for reducing the incidence or severity of dental caries comprising the isolated recombinant *Streptococcus mutans* strain of claim 1 and a pharmaceutically acceptable carrier.

* * * * *